(12) United States Patent
Rossel

(10) Patent No.: US 7,691,418 B2
(45) Date of Patent: Apr. 6, 2010

(54) COMPOSITION FOR INHIBITING OR PREVENTING THE FORMATION OF A BIOFILM

(75) Inventor: Bart Rossel, Nederzwalm (BE)

(73) Assignee: Oystershell NV, Drongen (BE)

( * ) Notice: Subject to any disclaimer, the term of this patent is extended or adjusted under 35 U.S.C. 154(b) by 311 days.

(21) Appl. No.: 11/663,119

(22) PCT Filed: Sep. 16, 2005

(86) PCT No.: PCT/EP2005/010011

§ 371 (c)(1),
(2), (4) Date: Apr. 2, 2007

(87) PCT Pub. No.: WO2006/029893

PCT Pub. Date: Mar. 23, 2006

(65) Prior Publication Data

US 2007/0258913 A1 Nov. 8, 2007

(30) Foreign Application Priority Data

Sep. 17, 2004 (BE) .................. 2004/0456

(51) Int. Cl.
*A61K 36/00* (2006.01)
(52) U.S. Cl. .................... 424/725
(58) Field of Classification Search ......... None
See application file for complete search history.

(56) References Cited

U.S. PATENT DOCUMENTS

| | | | |
|---|---|---|---|
| 3,525,626 A | 8/1970 | Swaine et al. | |
| 4,374,824 A | 2/1983 | Wahmi et al. | |
| 4,481,185 A * | 11/1984 | Grollier et al. | ................. 424/59 |
| 5,336,605 A | 8/1994 | Sakata et al. | |
| 5,571,501 A * | 11/1996 | Toy | .............................. 424/49 |
| 5,753,180 A | 5/1998 | Burger et al. | |
| 5,919,460 A | 7/1999 | Ingram et al. | |
| 6,238,671 B1 | 5/2001 | Joseph | |
| 6,340,468 B1 | 1/2002 | Cutler et al. | |
| 6,551,628 B1 | 4/2003 | Watson et al. | |
| 2001/0046525 A1 | 11/2001 | Bombardelli et al. | |
| 2003/0232763 A1 | 12/2003 | Jia | |
| 2004/0030301 A1 | 2/2004 | Hunter | |

FOREIGN PATENT DOCUMENTS

CN    1 363 634    8/2002

(Continued)

OTHER PUBLICATIONS

Wikipedia: RHEUM; online, URL<http://en.wikipedia.org/wiki/Rhubarb> pp. 1-5, accessed Jun. 15, 2009.*

(Continued)

*Primary Examiner*—Patricia Leith
(74) *Attorney, Agent, or Firm*—Knobbe, Martens, Olson & Bear, LLP

(57) ABSTRACT

Compounds for inhibiting and/or preventing the formation of a biofilm are disclosed. The compounds are an anthraquinone and/or a naphtoquinone, stereoisomeric forms, racemic mixtures, metabolites, esters or salts thereof, or mixtures thereof, and/or at least one plant extract including the compound or active fraction thereof. Compositions containing the compounds such as oral health products and methods of using the products in a method to prevent or inhibit biofilm formation are also disclosed. Preferred compositions include emodin and/or plant extracts from *Rheum* sp.

4 Claims, 12 Drawing Sheets

FOREIGN PATENT DOCUMENTS

| | | |
|---|---|---|
| EP | 1 479 295 | 11/2004 |
| GB | 768875 | 2/1957 |
| GB | 2 134 389 | 8/1984 |
| GB | 2 357 967 | 7/2001 |
| JP | 57-58612 | 4/1982 |
| JP | 58 057320 | 4/1983 |
| JP | 59 029620 | 2/1984 |
| JP | 59152311 A * | 8/1984 |
| JP | 03 287507 | 12/1991 |
| JP | 04 281763 | 10/1992 |
| JP | 05 238983 | 9/1993 |
| JP | 05 320039 | 12/1993 |
| JP | 06 065014 | 3/1994 |
| JP | 07 165598 | 6/1995 |
| JP | 08 151326 | 6/1996 |
| JP | 08 295632 | 11/1996 |
| JP | 09 012451 | 5/1997 |
| JP | 09 143042 | 6/1997 |
| JP | 10 114650 | 5/1998 |
| JP | 2000 001432 | 1/2000 |
| JP | 2000 044419 | 9/2000 |
| JP | 2002 187843 | 7/2002 |
| JP | 2003 155220 | 5/2003 |
| JP | 2004 196756 | 7/2004 |
| JP | 2005 206521 | 8/2005 |
| KR | 2004 003 200 | 1/2004 |
| SU | 685 979 | 9/1979 |
| WO | WO 99/11234 | 3/1999 |
| WO | WO 99/31295 | 6/1999 |
| WO | WO 01/28328 | 4/2001 |
| WO | WO 03/039503 | 5/2003 |
| WO | WO 03/099110 | 12/2003 |
| WO | WO 2004/045572 | 6/2004 |

OTHER PUBLICATIONS

Didry, et al. "Antimicrobial Activity of Some Naphthoquinones Found in Plants," *Annales Pharmaceutiques Francaises*, vol. 44, No. 1, pp. 73-78, 1986, Abstract.

Mustafa, et al. "Antimicrobial Activity of Acacia Nilotica Subspp. Nilotica Fruit Extracts," *Pharmacy and Pharmacology Communications*, vol. 5, No. 9, pp. 583-586 Sep. 1999, Abstract.

Kambizi, et al., "An Ethnobotanical Study of Plants Used for the Treatment of Sexually transmitted Diseases (Njovhera) in Guruve District, Zimbabwe," *Journal of Ethnopharmacology*, vol. 77, No. 1, pp. 5-9, Sep. 2001.

Alasbahi, et al. "Antimicrobial Activity of Some Yemeni Medicinal Plants," *Journal of Herbs, Spices and Medicinal Plants*, vol. 6, No. 3, pp. 75-83, 1999, Abstract.

Arias, et al. "Antibacterial Activity of Ethanolic and Aqueous Extracts of *Acacia aroma* Gill. ex Hook et Arn," *Life Sciences*, vol. 75, pp. 191-202, May 28, 2004.

Pepeljnjak, et al. "Antibacterial and Antifungal Activities of the Vitex agnus-castus L. Extracts," *Acta Pharmaceutica*, vol. 46, No. 3, pp. 201-206, 1996 Abstract.

Khan, M.R., "Antibacterial Activity of Some Tanzanian Medicinal Plants," *Pharmaceutical Biology 2001 Netherlands*, vol. 39, No. 3, pp. 206-212, 2001, Abstract.

Nie, et al., "A Method for Identifying Plant Extracts that Inhibit Biofilm Formation" 101st General Meeting of the American Society for Microbiology, May 20-24, 2001, Orlando, Florida, Abstract.

Glenn, et al. "Fdb1 and Fdb2, Fusarium Verticillioides Loci Necessary for Detoxification of Preformed Antimicrobials from Corn," *Molecular Plant-Microbe Interactions*, vol. 15, No. 2, pp. 91-101, Feb. 2002, Abstract.

Alves, et al. "Membrane-Related Effects Underlying the Biological Activity of the Anthraquinones Emodin and Barbaloin," *Biochemical Pharmacology*, vol. 68, pp. 549-561, Aug. 2004.

Didry, et al. "Activity of Anthraquinonic and Naphthoquinonic Compounds on Oral Bacteria," *Pharmazie 1994 Germany*, vol. 49, No. 9, pp. 681-683, 1994 Abstract.

Ole-Miaron, J.O., "The Maasai Ethnodiagnostic Skill of Livestock Diseases: A Lead to Traditional Bioprospecting," *Journal of Ethnopharmacology*, vol. 84, No. 1, pp. 79-83, Jan. 1, 2003.

Suffredini, et al. "Screening of Antibacterial Extracts from Plants Native to the Brazilian Amazon Rain Forest and Atlantic Forest," *Brazilian Journal of Medical and Biological Research*, vol. 37, No. 3, pp. 379-384, Mar. 2004.

Nabiha, et al. "Antimicrobial Activity of Essential Oils from Tunisian Aromatic Plants," *Flavour and Fragrance Journal*, vol. 18, No. 5, pp. 380-383, 2003, Abstract.

Abdulaziz, A.M., "Studies on the Antimicrobial Activity of *Juglans regia*," *American Journal of Chinese Medicine*, vol. 25, No. 2, pp. 175-180, 1997, Abstract.

Alzoreky, et al., "Antibacterial Activity of Extracts from Some Edible Plants Commonly Consumed in Asia," *International Journal of Food Microbiology*, vol. 80, No. 3, pp. 223-230, Feb. 15, 2003, Abstract.

Mishurova, et al., "Essential Oil in Vitex-Agnus-Astus L. Its Component Composition and Antimicrobial Activity," *Rastitel'nye Resursy*, vol. 22, No. 4, pp. 526-530, 1986, Abstract.

Pai, et al. "Evaluation of Antiplaque Activity of *Azadirachta indica* Leaf Extract Gel: A 6-Week Clinical Study," *Journal of Ethnopharmacology*, vol. 90, No. 1, pp. 99-103, Jan. 2004, Abstract.

de Almeida, et al, "Toothbrushing with Vegetable Oil: A Clinical and Laboratorial Analysis," *Pesquisa Odontológica Brasileira (Brazilian Oral Research)*, vol. 18, No. 2, pp. 168-173, Apr. 2004, Abstract.

Peng, et al., Therapeutic Use of Garlic Juice in Periodontal Diseases, *Hunan Yike Daxue Zuebao*, vol. 16, No. 2, pp. 181-183, 1991, Abstract.

Goldaru Pharmaceutical Laboratory: "Sankol (Herbal Drop)." Retrieved from the Internet on Mar. 6, 2006 at URL: http://www.goldaru-co.com/products/sankol.htm (secondarily retrieved Mar. 14, 2007).

International Search Report dated Mar. 7, 2006.

Goldaru Pharmaceutical Laboratory: "Sankol (Herbal Drop)." Retrieved from the Internet on Mar. 6, 2006 at URL: http://www.goldaru-co.com/products/sankol.htm.

Baehni, et al. "Anti-Plaque Agents in the Prevention of Biofilm-Associated Oral Diseases," *Oral Diseases*, vol. 9 (Suppl. 1), pp. 23-29, 2003.

Yiamkamnuan, et al. "Inhibitory Effect of some Active Ingredients of Thai Herbs on *Streptococcus mutans*," (Abstract) Supported by Dental Research Fund, Dental research project 3205-312 #37/2002 Faculty of Dentistry, Chulalong University, 2 pages, site update Jan. 5, 2005.

Murthy, et al. "Biofilm Control for Plate Heat Exchangers using Surface Seawater from the Open Ocean for the OTEC Power Plant," *International Biodeterioration & Biodegradation*, vol. 53, pp. 133-140, 2004.

* cited by examiner

COMPOSITION FOR INHIBITING OR PREVENTING THE FORMATION OF A BIOFILM

RELATED APPLICATIONS

This application is the U.S. National Phase under 35 U.S.C. 371 of International Application PCT/EP2005/010011, filed Sep. 16, 2005, which claims priority to BE 2004/0456, filed Sep. 17, 2004.

TECHNICAL FIELD

In a first aspect the present invention relates to a plant extract which shows a pharmacological activity, and more particularly a biofilm inhibitory activity, and active fractions and active compounds that can be prepared or isolated hereof. The invention also provides a composition and an oral health product for inhibiting or preventing the formation of a biofilm, especially in the oral cavity.

BACKGROUND

The characteristic of microorganisms to form biofilms on surfaces, gives numerous problems. The biofilm is a collection of microcolonies with water channels in between and an assortment of cells and extra cellular polymers (glycoproteins, polysaccharides and proteins). Once the microorganisms (bacteria) adhere, they can multiply, form complex multilayered colonies, and produce a slimy matrix material that encases the bacterial cells.

In nutrient-limited ecosystems, such as the aquatic environments, bacteria have a marked tendency to attach to surfaces and initiate the formation of a biofilm. Biofilms routinely foul ship hulls, submerged oil platforms, and the interiors of pipe works and cooling towers. The damage caused by these wildly procreating bacteria includes corrosion and failure of metal components.

Biofilm formation is also a serious medical problem that manifests itself as biomaterial-associated infections of devices such as endotracheal tubes, intravenous catheters, urinary catheters, and contact lenses, and of prosthetic implants. In fact, the increased use of biomedical devices and implants in humans in recent years has resulted in a concomitant rise in bacterial infections. Depending on the organism involved, these infections can be acute (symptoms appear relatively soon after material insertion) or chronic (may take months for symptoms to appear). The formation of a biomaterial-associated biofilm (irreversible infection) usually leads to removal or revision of the affected device or implant, with obvious devastating results for the patient.

Further, biofilms are also a severe problem in oral health since they can cause dental diseases including dental plaque. Dental plaque is the result of adhesion and colonization by different bacteria on the dental surface. Dental plaque consists of a three-dimensional organized dynamic structure of one or more microorganism species, which are irreversibly attached to the dental enamel, whereon they form an extracellular matrix. This type of biofilm mainly appears in between and at the bottom of the teeth (against the gums) where the mechanical removal is hampered. The biofilm mainly consists of bacteria, extra-cellular polysaccharides (EPS=biofilm matrix) and water. This biofilm may lead to tooth demineralization, gingivitis, periodontitis and even systemic complications.

Immediately after brushing one's teeth a conditioning film arises on the tooth surface that mainly consists of saliva elements and food remainders. Primary oral bacterial colonizers, especially Streptococci, e.g. *Streptococcus mutans, S. sanguinis, S. mitis. S. sobrinus* and *S. salivarius*, attach to this conditioning film. These bacteria convert sucrose into sticky glucans onto the dental surface. These bacteria produce extra-cellular glucosyltransferases (GTF), enzymes that catalyze the splitting of sucrose into fructose and glucose. Fructose can further be converted into lactate, which results in an oral pH drop that can lead to reversible solution of calcium ions and demineralization of the dental surface. Glucose is transferred to a glucose polymer (dextran chain) and thus forms part of the extra-cellular polysaccharides (EPS), which form an ideal culture medium for a dental biofilm. Other bacteria find shelter in this biofilm and may become sedentary. The said bacteria ferment food remains, which results in a decreased oral pH and leads to a demineralization of the dental surface. When the pH recovers, calcium mineralizes back out of the saliva to the dental enamel and eventual calcify the dental plaque into a persistent dental tartar or calculus.

The development of effective agents for controlling microorganism biofilms adherent to cell surfaces has proven problematic. A biofilm is in part difficult and often impossible to eradicate with antibiotics, in part because the slime matrix acts as a physical and chemical barrier to protect the bacteria. Antimicrobial agents such as antibiotics and other drugs inhibiting bio-adhesion are often not able to remove the biofilm.

In the case of dental plaque for instance, current treatment consists of mechanical removal and/or chemical killing of biofilm bacteria. In the latter treatment, all germs in the oral flora are killed, which leads to a disruption of the natural, microbial oral homeostasis. Moreover, such treatment has the disadvantage that, by killing biofilm bacteria, the released ecological niche can be occupied by detrimental yeast species and/or fungi, e.g. Candida sp.

Another problem in treating biofilm is the occurrence of resistance of biofilm bacteria against antimicrobial agents. It is troubling that the biofilm phenotype of some species has been shown to differ radically from the planktonic phenotype of the same organism. One of the facets in which biofilm bacteria differ the most profoundly from their planktonic counterparts, is in the critical matter of resistance to antibacterial agents. Biofilm cells are more resistant than planktonic cells. This is believed to be due to more than just a physical protection by the biofilm matrix. Bacteria in biofilm seem to posses an altered physiology and mode of growth. Bacteria in biofilm are all together a distinct phenotype with altered gene expression as compared to the same species in planktonic phase.

In view of the above, it can be seen that there remains a great need in the art for compositions and methods able to prevent or inhibit the formation of biofilms.

It is therefore a main object of the present invention to provide effective compounds, compositions, and methods for preventing and/or inhibiting biofilm formation.

It is yet another object of the invention to provide compounds, compositions for preventing and/or inhibiting biofilm formation, which are not bactericidal.

It is a preferred object of the invention to provide effective compounds, compositions, and methods for preventing and/or inhibiting biofilm formation on dental surfaces in the oral cavity. More particularly, it is an object of the present invention to provide an improved oral health product, which prevents or inhibits dental biofilm formation.

In another object, the present invention aims to provide compounds, compositions, and methods for the treatment and/or prevention of dental plaque, dental tartar and/or dental diseases related thereto.

SUMMARY

The present invention is at least partially based on the finding that extracts of one or more of the below mentioned plants, active compounds and active fractions prepared or isolated thereof, show a pharmacological activity, and in particular a biofilm inhibitory activity.

In a first aspect, the present invention therefore relates to the use of at least one compound selected from the group comprising an anthraquinone and a naphtoquinone, stereoisomeric forms, racemic mixtures, metabolites, esters or salts thereof, or mixtures thereof, and/or of at least one plant extract or active fraction thereof comprising said compound for preventing and/or inhibiting biofilm formation. In a preferred embodiment, the invention relates to the use of said compound or extract or active fraction thereof, for preventing and/or inhibiting the formation of biofilm in the oral cavity.

In another aspect, the present invention therefore relates to the use of at least one compound selected from the group comprising an anthraquinone and a naphtoquinone, stereoisomeric forms, racemic mixtures, metabolites, esters or salts thereof, or mixtures thereof, and/or of at least one plant extract or active fraction thereof comprising said compound for treating a biofilm. In a preferred embodiment, the invention relates to the use of said compound or extract or active fraction thereof, for treating a biofilm in the oral cavity.

In another preferred embodiment, the invention relates to the use of at least one plant extract or active fraction thereof comprising said compound whereby the plant extract is obtained from one or more plants selected from the group comprising *Acacia* sp., *Agnus* sp., *Aloe* sp., *Alium* sp., *Amygdalus* sp., *Azadirachta* sp., *Angelica* sp. *Barosma* sp., *Cassia* sp., *Centella* sp., *Cerasus* sp., *Ceratonia* sp., *Chamomilla* sp., *Chimaphila* sp., *China rubra* sp., *Cinnamomum* sp., *Citrus* sp., *Cochlearia* sp., *Jateorhiza* sp., *Eugenia* sp., *Fagopyrum* sp., *Panax* sp., *Haematoxylum* sp., *Hammamelis* sp., *Hypericum* sp., *Juglans* sp., *Lavendula* sp., *Lycopus* sp., *Mentha* sp., *Myrtus* sp., *Oenothea* sp., *Origanum* sp., *Phyllantes* sp., *Podophylum* sp., *Polygonatum* sp., *Polygonum* sp., *Prunus* sp., *Punica* sp., *Rhamnus* sp., *Rheum* sp., *Rubus* sp., *Rumex* sp., *Salvadora* sp., *Simarouba* sp., *Solanum* sp., *Sorbus* sp., *Terminalia* sp., *Thymus* sp., *Uva-ursi* sp., *Vitis* sp., *Woodfordia* sp., *Zea* sp., or any combinations thereof.

In another preferred embodiment, the above-mentioned compounds are applied at a concentration which is not bactericidal. The use of bactericidal antimicrobial means can induce bacterial resistance. Such problem is avoided in the present invention in an advantageous manner by using compounds as defined herein that substantially inhibiting biofilm formation at relatively low, non-bactericidal doses.

In another aspect the invention provides a composition for preventing and/or inhibiting the formation of a biofilm, comprising an effective amount of at least one compound selected from the group comprising an anthraquinone and a naphtoquinone, stereoisomeric forms, racemic mixtures, metabolites, esters or salts thereof, or mixtures thereof, and/or of a plant extract or active fraction thereof comprising said compound, as defined in herein. Preferably, the effective amount of said compound or extract or active fractions is an amount, which has not bactericidal effect.

In a further aspect, the invention thus provides an oral health product for preventing and/or inhibiting the formation of a biofilm which comprises one or more compounds selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein, or composition as defined herein. The oral health product may include a gel, a paste, a gum, a stick pill, a rinsing liquid, a toothpaste, a strip a tablet, soluble tablet or similar, a topical medicament, an oral dentifrice, an injectable composition, an oral tablet, a lozenge or a soft gelatin capsule.

In yet another aspect the invention is directed to the use of a compound selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein, for the preparation of a medicament for preventing and/or inhibiting biofilm formation.

The present invention also relates to a method for preventing and/or inhibiting biofilm formation comprising administering an effective amount of one or more compounds selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein or a composition as defined herein.

In the broadest aspect, the invention is thus directed to a non-bactericidal or non-bacteriostatical use of the herein defined active compound(s), extract(s), or active fraction(s) thereof, or composition(s) and a non-bactericidal or non-bacteriostatical method for preventing or inhibiting the formation of a biofilm.

With the insight to better show the characteristics of the invention, some preferred embodiments and examples are described hereafter referring to the enclosed figures.

DETAILED DESCRIPTION OF THE INVENTION

Figure 1:
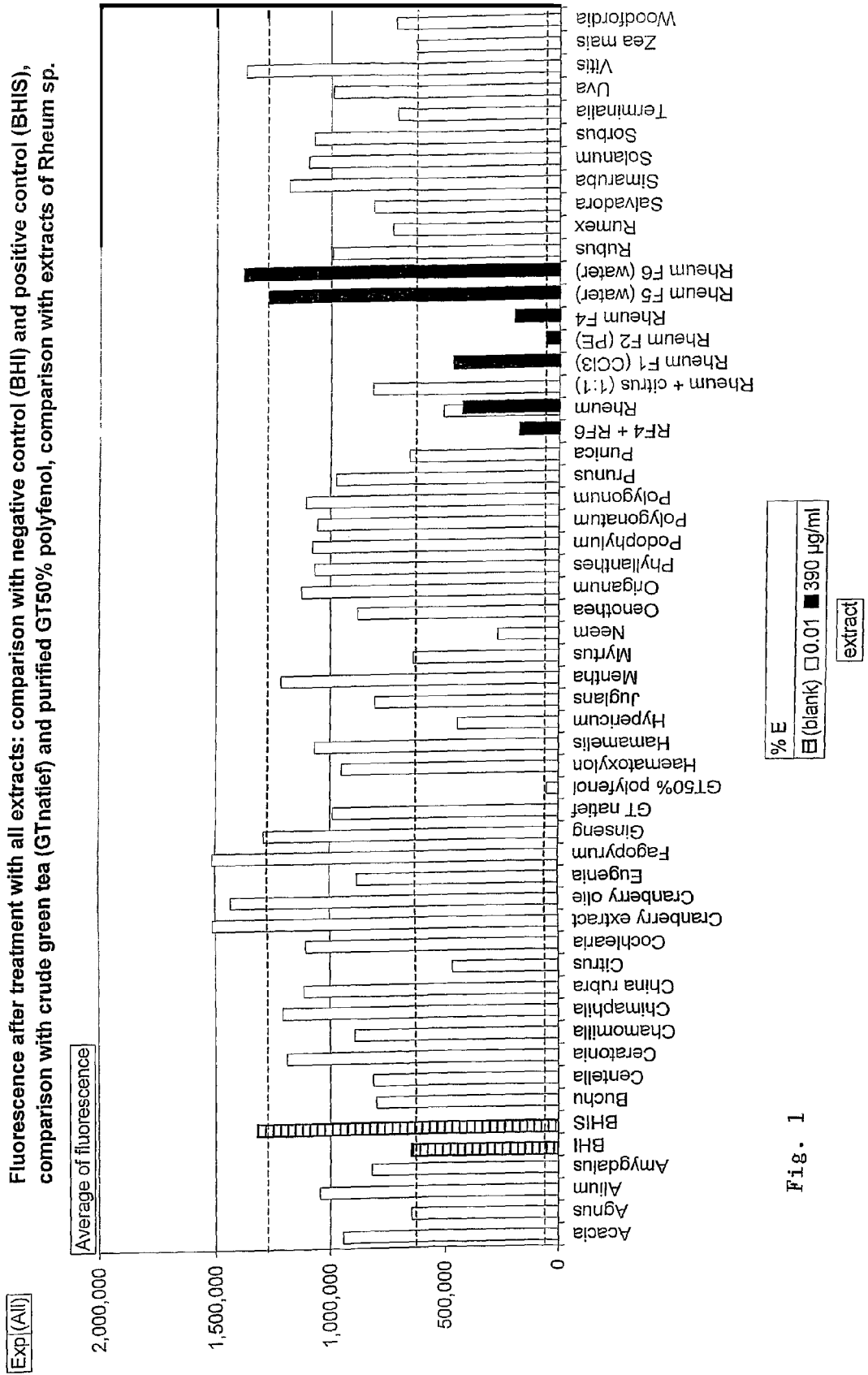
FIG. 1 illustrates fluorescence values of stained biofilms irrigated with a plant extract according to the present invention, or fractions thereof. Fluorescence values of the plant extracts are compared with a) a negative (BHI) and a positive (BHIS) control, b) a crude green tea extract (GT native) and a purified green tea extract standardized at 50% polyphenols f and c) different *Rheum* extract fractions.

The present invention advantageously provides for compounds, compositions and methods for preventing and/or inhibiting biofilm formation without having to resort to bactericidal, disinfecting and/or antibiotic drugs with their accompanying disadvantages. The present invention also advantageously provides for compounds, compositions and methods for treating a biofilm formation. The term "biofilm" as used herein refers to a biological film that mainly consists of bacteria, extra-cellular polysaccharides (EPS=biofilm matrix) and water. A biofilm, as referred to herein, may include a biofilm which is formed and attached to any kind of abiotic surface including a dental surface, but also surface of medical devices such as tubes, catheters including intravenous catheters, urinary catheters; contact lenses; any kind of prosthetic implants such as heart valves, joint replacements, dental implants, and spinal implants, etc. . . . , or even surfaces on non-medical devices such as pipes, tubes, towers, columns, etc. . . . . The term biofilm may also include a biological film which is formed and attached on biotic surfaces such as human or animal cells from body parts or organs, such as the skin, urinary or other tracts, parts or regions of the ear, lung, etc. . . . .

The present compounds, compositions and methods are particularly suitable for preventing and/or inhibiting the formation of a biofilm, or for treating biofilm on teeth surface in the oral cavity. In view hereof, the present compounds, compositions and methods are also particularly suitable for preventing and/or treating dental plaque, dental tartar, and/or dental diseases related thereto.

Dental plaque consists of a three-dimensionally organized dynamic structure of one or more species of microorganisms which are capable of irreversibly attaching to the dental enamel and forming an extra-cellular matrix hereon. This type of biofilm mainly occurs in between and at the bottom of the teeth (against the gums) where mechanical removal is hampered. The biofilm generally consists of bacteria, extra-cellular polysaccharides (EPS=biofilm matrix) and water. The biofilm matrix is not only of importance for the adhesion and biofilm stabilization, but also ensures heterogeneity and nutrient collection in the biofilm. In addition, the biofilm further contains water channels for protection of the microorganisms against dehydration and transport of soluble nutrients to the inner regions of the biofilm.

Dental tartar is a film that covers teeth consisting of calcium phosphate and carbonate, food particles and other organic matter, or is basically mineralized plaque. The tartar will stick to the tooth surface forming a scaffold for more plaque accumulation. The continued build-up of tartar both above and below the gum line can eventually produce an environment that is a haven for certain types of bacteria that may be more destructive to the periodontal tissues and also produce a more noticeable odor. This can lead periodontal disease.

Dental diseases, which may be related to dental plaque comprise but are not limited to dental caries, gingivitis, periodontitis, systemic infections, etc. . . . . . Tooth decay or dental caries is provoked by a dental demineralization by acids. The acid is produced by the bacterial flora in the deeper layers of dental plaque, fermenting carbohydrates (starch and sugars), such that pH drops and the dental tissue dissolves. Gingivitis is an infection of the gums. When the dental plaque, initially arising on the dental enamel, grows further into the gingiva (=the gums), infection of the gum may occur. An infection of the gums can expand from the edge of the gums to the underlying jawbone. Consequently the jawbone gets lost around the teeth and molars. Finally that much jawbone may disappear such that teeth and molars come loose and finally fall out. This type of gums infection is called periodontitis. Infection of the gums is very cumbersome but should in particular be prevented in patients suffering from rheumatism and/or having heart valves since bacteria can penetrate the blood stream, attaching themselves to the joints, heart valves, etc. . . . to form biofilms hereon, which in turn give rise to systemic infections.

This present invention is at least partially based on an extensive research directed to the identification and characterization of one or more substances applicable for the inhibition of biofilms, and further also in the treatment of dental plaque. It has now surprisingly been found that active compounds as defined herein, and in particular compounds having formula I according to the present invention (see below), or plants extracts or fractions thereof containing these compounds, have a potent biofilm-inhibitory activity. According to the present invention the terms "anti-biofilm activity", "biofilm-inhibiting activity" or "biofilm-inhibitory effect" or "biofilm-inhibitory activity" or the like, are defined herein as the ability of the compounds as defined in the present invention to inhibit, prevent, or greatly reduce the formation or outgrowth of a biofilm in vitro as well as in vivo.

More particularly, in accordance with the present invention, plant extracts were identified which are able to inhibit first phase bacterial surface attachment, in particularly of dental surface. In addition, in accordance with the present invention also active compounds, which are particularly suitable for inhibiting biofilm formation were identified and characterized. The present invention reports on the use of these active compounds and extracts containing such compounds, e.g. in an oral health product, or food product or other products, for preventing and/or inhibiting the formation of biofilms or for treating a biofilm and for the treatment and/or prevention of biofilm-related diseases, including but not limited to dental plaque, dental tartar, and/or dental diseases related thereto.

The present description is directed to the inhibition or prevention of biofilm formation on dental surfaces in the oral cavity. However, it shall be understood that the present invention is not restricted thereto, and that the herein disclosed compounds, extracts, extract fractions, compositions or products are equally applicable for inhibiting and/or preventing biofilm formation on other kind of surfaces and under other type of conditions.

Compounds

In first embodiment, the invention relates to the use of at least one compound selected from the group comprising an anthraquinone and a naphtoquinone, stereoisomeric forms, racemic mixtures, metabolites, esters or salts thereof, or mixtures thereof, and/or of at least one plant extract or active fraction thereof comprising said compound for preventing and/or inhibiting biofilm formation. In a preferred embodiment, the invention relates to a compound having formula I

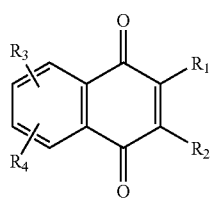

formula I stereoisomeric forms, racemic mixtures, metabolites, esters or salts thereof, or mixtures thereof, wherein $R_3$ and $R_4$ are independently selected from the group comprising hydrogen, alkyl, hydroxyl, carboxyl, hydroxyalkyl, and a glycosyl moiety, and wherein $R_1$ and $R_2$ are independently selected from the group comprising hydrogen, alkyl, alkenyl, or wherein $R_1$ and $R_2$ together with the atoms to which they are attached form an aromatic ring, which is optionally substituted with one or more substituents independently selected from the group comprising hydrogen, alkyl, hydroxyl, carboxyl, hydroxyalkyl and a glycosyl moiety.

It has been shown that compounds selected from the group comprising an anthraquinone and a naphtoquinone, and/or a plant extract or active fraction thereof comprising said compound, show a disturbing activity (effect) on bacterial biofilm formation, without being bactericidal.

The inhibition of biofilm formation can—at least partially—be explained by the fact that at least some of the herein-mentioned plant extracts, active fractions or active compounds thereof may show a GTF inhibitory activity. The (bacterial) GTF-enzyme catalyses the conversion of sucrose into fructose and glucose, two monosaccharides that contribute to dental plaque formation and thereto related dental diseases. Glucose is transferred to a glucose polymer, called glycan or dextran and is thus part of extra-cellular polysaccharides (EPS) that form an ideal culture medium for micro-organisms into the dental biofilm. Fructose is converted to lactate, whereby the resulting pH drop leads to a demineralization of the dental surface. Inhibition of GTF activity allows inhibition of both above-mentioned processes. More particularly by inhibiting or captivating the glycosyltransferase enzyme, the adhesion of extra-cellular polysaccharides onto the dental surface can be strongly inhibited, and thus the formation of a biofilm matrix can be strongly inhibited. Consequently, dental plaque formation and the occurrence of thereto related diseases can thus be reduced.

Moreover herein-mentioned plant extracts, active fractions or active compounds thereof, are appropriate to inhibit biofilm formation on dental surfaces by a mechanism that differs from a GTF-inhibitory activity. This activity can be based on inhibition of enzymes different from the GTF enzyme that plays a role in dental plaque formation, e.g. enzymes that play a role in the formation of saccharide polymers and thus in the formation of extra-cellular polysaccharides (EPS). This activity can be based on inhibition of virulence factors that promote the survival of the biofilm such as, in the case of S. mutans, the capacity to produce acids and the capacity to withstand a very acid environment. On the other hand this activity can also be based on the specific interaction between plant extracts and biofilm "quorum sensing" mechanisms such as but not limited to the presently known systems as auto-inducer I (N-acyl homoserine lactone analogues), auto-inducer II (lux S expression) and Competence Stimulating Peptides. By these mechanisms, micro-organisms auto-regulate their number and the transition of latent presence to virulent presence in the biofilm. Above-mentioned extracts, active fractions or active compounds thereof, can exert a disturbing activity hereon. Use of the present compounds provides thus a way to interfere with the bacterial communication processes that take place in human and animals. These compounds may advantageously interfere with the signaling in bacterial communities. Secondary to the said mechanisms, in particular the quorum-sensing mechanism, these compounds may also affect the consequent release of bactericins such as mutacin in the case of S. mutans. Use of the present compounds, extract or fractions thereof thus makes it possible to hamper harmful bacterial action.

Whenever used in the present invention the term "active compound" or compounds of the invention" or a similar term is meant to include the compounds of general formula I and any subgroup thereof.

This term also refers to the compounds of general formula I and their N-oxides, salts, stereoisomeric forms, racemic mixtures, pro-drugs, esters and metabolites, as well as their quaternized nitrogen analogues.

The term "stereoisomeric forms" of compounds of the present invention, as used herein, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers forms of the basic molecular structure of said compound. All stereochemically isomeric forms of the compounds of the present invention either in substantially pure form or in admixture with each other are intended to be embraced within the scope of the present invention.

The term "diastereomers" refers to stereoisomers that are not enantiomers; i.e. that have different chemical and physical properties. The term "enantiomers" refers to compounds which are non-superimposable, i.e. which have different mirror images; but having a vast majority of chemical and physical properties being identical. The term "racemic mixture" refers to mixtures of enantiomers, diastereomers or combinations thereof.

Pure stereoisomeric forms of the compounds as mentioned herein are defined as isomers substantially free of other enantiomeric or diastereomeric forms of the same basic molecular structure of said compounds. In particular, the term 'stereoisomerically pure' concerns compounds having a stereoisomeric excess of at least 80% (i. e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula I can be obtained separately by conventional methods. Appropriate physical separation methods which may advantageously be employed are, for example, selective crystallization and chromatography, e.g. column chromatography.

The term "metabolite" according to the present invention refers to a product or a anthraquinone or naphtoquinone compound which is the result of metabolism, i.e. the result of physical an/or chemical processes by which the product is produced, maintained or destroyed.

The term "esters" according to the invention includes the conventional non-toxic esters which are formed, e.g., from inorganic or organic acids. Examples of such acid addition esters include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, erucate, ethanesulfonate, ferulate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, undecanoate and valerate.

The term esters as used in the present invention is meant to include esters, as defined above, that can be isolated or derived from plants as defined herein. It shall be understood that this term also includes esters that can be chemically synthesized according to techniques that are known in the art.

For therapeutic use, the "salts" of the compounds of formula I are those wherein the counter-ion is pharmaceutically or physiologically acceptable. However, salts having a pharmaceutically unacceptable counter-ion may also find use, for example, in the preparation or purification of a pharmaceutically acceptable compound of formula I. All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The compounds of formula I containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms which the compounds of the present invention are able to form. Examples of such forms are e.g. hydrates, alcoholates and the like.

The term "substantially pure" as used herein refers to a purity of more than 80% and preferably more than 90% and more preferred more than 99%.

The N-oxide forms of said compounds are meant to comprise compounds wherein one or several nitrogen atoms are oxidized to the so-called N-oxide. These terms are used herein to refer to a compound according to the invention that has an activity superior or similar to the extract's activity, particularly a biofilm inhibitory activity and/or an anti-GTF activity.

The compounds according to the invention can be present in a plant extract or active fraction thereof as defined herein and isolated or derived there from plants, as explained below. It is to be understood that these active compounds can be derived or isolated from all parts of the plants, as mentioned herein, including leafs, seeds, roots, branches, shoots, etc. . . . . . It shall be understood that the terms active compound or compounds of the invention also encompass compounds according to the invention that are not derived from plants as such but that are chemically synthesized according to techniques that are known in the art. In a preferred embodiment the invention relates to compounds, as defined herein, which naturally occurs in plants, such as those enumerated herein, and which can be isolated thereof. In another preferred embodiment the invention relates to compounds, as defined herein, which are synthetically prepared.

The term "active fraction" as used herein thus refers to a fraction of a plant extract according to the invention that has an activity similar to the activity of the extract, particularly a biofilm inhibitory activity and/or an anti-GTF activity. The fraction can be a polar fraction, an apolar fraction or any combinations hereof.

Whenever the term "substituted" is used in the present invention, it is meant to indicate that one or more hydrogens on the atom indicated in the expression using "substituted" is replaced with a selection from the indicated group, provided that the indicated atom's normal valance is not exceeded, and that the substitution results in a chemically stable compound, i.e. a compound that is sufficiently robust to survive isolation to a useful degree of purity from a reaction mixture, and formulation into a therapeutic agent.

The term "alkyl", alone or in combination, means straight and branched chained saturated hydrocarbon radicals containing from 1 to 30 carbon atoms, preferably from 1 to 15 carbon atoms, more preferably 1 to 10 carbon atoms. Examples of such radicals include methyl, ethyl, n-propyl, isopropyl, n-butyl, isobutyl, sec-butyl, tert-butyl, 2-methylbutyl, pentyl, iso-amyl, hexyl, 3-methylpentyl, octyl and the like.

The term "alkenyl", alone or in combination, defines straight and branched chained hydrocarbon radicals containing from 2 to about 30 carbon atoms, preferably 2 to 18 carbon atoms, preferably from 2 to 8 carbon atoms, more preferably 2 to 6 carbon atoms containing at least one double bond such as, for example, ethenyl, propenyl, butenyl, pentenyl, hexenyl and the like.

As used herein, the term "carboxyl" or "—COOH" is an acid moiety whereby the carbon atom binds to the carbon atom to which it is attached.

As used herein the term "hydroxyalkyl" embraces linear or branched alkyl groups having 1 to 30 carbon atoms, preferably from 1 to 15 carbon atoms, more preferably 1 to 10 carbon atoms, any one of which may be substituted with one or more hydroxyl groups.

The term glycosyl moiety as used herein refers to a saccharyl moiety such as but not limited to mono-, di-, oligo-, or a poly-saccharide moiety, a hydroxysubstituted cyclohexyl moiety, the amino, amido, thio, carboxy or hydroxyl-protected derivatives thereof, and can be optionally substituted by one or more substituents. The term "glycosyl" as used herein encompasses stereoisomers, optical isomers, anomers and epimers of said glycosyl moiety. Thus a hexose moiety can for instance be either an aldose or a ketose moiety, can be of D- or L-configuration, can assume either α or β conformation, and can be dextro- or levo-rotatory with respect to plane-polarized light. A "saccharyl moiety" as used herein refers to monosaccharides, di-, tri-, oligo- or poly-saccharides. Exemplary monosaccharide moiety preferably includes, but is not limited to a pentosyl, hexosyl or a heptosyl. Preferred examples comprise glucosyl, fructosyl, galactosyl, mannosyl, ribosyl, ribulosyl, arbinosyl, rhamnosyl, and apiosyl, As used herein before, the term "one or more" covers the possibility of all the available C-atoms, where appropriate, to be substituted, preferably, one, two or three. When any variable, e.g. alkyl, occurs more than one time in any constituent, each definition is independent.

A particular group of compounds are those compounds of formula I wherein $R_3$ and $R_4$ are independently selected from the group comprising hydrogen, alkyl, hydroxyl, carboxyl, and hydroxyalkyl, and wherein $R_1$ and $R_2$ together with the atoms to which they are attached form an aromatic ring, which is substituted with one or more substituents independently selected from the group comprising hydrogen, alkyl, hydroxyl, carboxyl, and hydroxyalkyl.

In a preferred embodiment, the compounds of the invention are represented by formula II

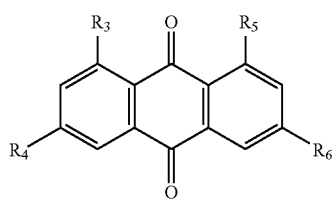

formula II stereoisomeric forms, racemic mixtures, metabolites, esters or salts thereof, or mixtures thereof, wherein $R_3$, $R_4$, $R_5$ and $R_6$ are independently selected from the group comprising hydrogen, alkyl, hydroxyl, carboxyl, hydroxyalkyl and a glycosyl moiety. A particular group of compounds are those compounds of formula II wherein $R_3$ and $R_4$ are independently selected from the group comprising hydrogen, $CH_3$, OH, $CO_2H$, or $CH_2OH$, and wherein $R_5$ and $R_6$ are independently selected from the group comprising hydrogen, alkyl, hydroxyl, carboxyl, hydroxyalkyl and a glycosyl moiety.

In a preferred embodiment, the invention relates to the use of compounds, plant extracts or active fractions thereof comprising said compounds, which have formula II, wherein $R_3$, $R_4$, $R_5$ and $R_6$ are independently selected from the group comprising hydrogen, $CH_3$, OH, $CO_2H$, or $CH_2OH$.

In a particularly preferred embodiment, the invention relates to the use of compounds, plant extracts or active fractions thereof comprising said compounds, which are represented by formula II, wherein $R_4$ and $R_6$ are independently selected from the group comprising hydrogen, alkyl, hydroxyl, carboxyl, and hydroxyalkyl, and preferably from the group comprising hydrogen, $CH_3$, OH, $CO_2H$, or $CH_2OH$, and wherein $R_3$ and $R_5$ are OH.

In a particularly preferred embodiment the compounds are selected from the group comprising aloe-emodin, chrysophanol, emodin, and rhein or any combinations thereof, and most preferably emodin.

Another particular group of compounds are those compounds according to formula I, stereoisomeric forms, racemic mixtures, metabolites, esters or salts thereof, or mixtures thereof, wherein $R_3$ and $R_4$ are independently selected from the group comprising hydrogen, alkyl, hydroxyl, carboxyl, and hydroxyalkyl, wherein $R_2$ is methyl, and wherein $R_1$ is selected from the group comprising hydrogen, alkyl, and alkenyl. In a preferred embodiment the invention also relates to compounds of formula III,

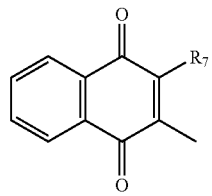

formula III stereoisomeric forms, racemic mixtures, metabolites, esters or salts thereof, or mixtures thereof, wherein $R_7$ is equal to $R_1$ and selected from the group comprising hydrogen, alkyl, or alkenyl. In a particularly preferred embodiment these compounds include vitamin K 1 (phytomenadione), vitamin K2 (menaquinone), and vitamin K3 (2-methyl-napthoguinone and most preferably vitamin K3.

In another embodiment the invention relates to the use of at least one compound selected from the group comprising quinone, a hydroquinone, a hydroxyquinone, a benzoquinone, an anthraquinone, a naphtoquinone, an anthrone, a dianthrone, a naphtodianthrone, a benzanthrone, stereoisomeric forms, racemic mixtures, metabolites, esters or salts thereof, or mixtures thereof, and/or of at least one plant extract or active fraction thereof comprising said compound for preventing and/or inhibiting biofilm formation, or for treating a biofilm.

In a even more preferred embodiment said compound is selected from the group comprising but not limited to rheinosides A/B, aloins A/B, rhein-8-glucoside, hypericin, xanthone, coenzyme Q10, (N-anthraquinonyl-1)-delta-aminovaleric acid; 1,2,4-trihydroxy-9,10-anthracenedione; 1,2-diaminoanthraquinone; 1,3,6-trihydroxy-2-methyl-9,10-anthraquinone-3-O-(6'-acetylglucoside); 1,3,6-trihydroxy-8-(3-methylbutyl)anthraquinone; 1,3,6-trihydroxy-8-n-butylanthraquinone; 1,3,6-trihydroxy-8-n-pentylanthraquinone; 1,3,6-trihydroxy-8-n-propylanthraquinone; 1,4-anthraquinone; 1,4-bis(2,3-epoxypropylamino)-9,10-anthracenedione; 1,4-bis (isopropylamino)anthraquinone; 1,4-diamino-2,3-dichloroanthraquinone; 1,4-diaminoanthraquinone; 1,4-dihydroanthraquinone; 1,4-dihydroxyanthraquinone; 1,4- dimethoxy-2-hydroxyanthraquinone; 1,6,8-trihydroxy-3-methylanthraquinone; 1-O-rhamnosyl(1-2)glucoside; 1,6-dihydroxy-2,4-dimethoxyanthraquinone; 1,6-dihydroxy-2-methoxyanthraquinone; 1,8,1',8'-tetrahydroxybisanthrone; 1,8-bis(2-diethylaminoethylamino)anthracene-9,10-dione; 1,8-dihydroxy-4-hydroxymethylanthraquinone; 1-(omega-diethylaminopropylamide)-2-methoxy-4-hydroxy-9,10-anthracenedione; 1-(omega-diethylaminopropylamido)-4-hydroxy-9,10-anthracenedione; 1-amino-2,4-dibromoanthraquinone; 1-amino-2-methylanthraquinone; 1-amino-4-hydroxyanthraquinone; 1-aminoanthraquinone; 1-hydroxy-6,7,8-trimethoxy-3-methylanthraquinone; 1-hydroxyanthraquinone; 1-hydroxyserirubicin; 1-piperidinoanthraquinone; 2,6-dihydroxyanthraquinone; 2,7,8-trihydroxyanthraquinone; 2-(hydroxymethyl)anthraquinone; 2-aminoanthraquinone; 2-azidoanthraquinone; 2-methyl-1-nitroanthraquinone; 2-methylanthraquinone; 3',4'-dehydro-4'-deoxydothistromin; 3-(2-hydroxyethylamino)methyl-1,8-dihydroxy-9,10-anthraquinone; 3-bis((2-chloroethyl)amino)methyl-1,8-dihydroxy-9,10-anthraquinone; 3-methoxybenzo(a)anthracene-7,12-; 4-deoxybostrycin; 4a,9a-epoxy-4a,9a-dihydroanthracene-1,4,9,10-tetrone; 5'-hydroxyaverantin; 5,8-bis(2-aminoethylamino)-1-azaanthracene-9,10-dione; 5-hydroxydamnacanthol-omega-ethyl ether; 7,7'-biphyscion; 8,11-bis((2-((2-hydroxyethyl)amino)ethyl)amino)-6-methoxy-1,2,3,4-tetrahydro-7,12-benz(a)anthraquinone; 8-hydroxydamnacanthol-omega-ethyl ether; 8-hydroxysubspinosin; 8-O-methylrabelomycin; 9,10-anthraquinone; 9,10-anthraquinone; 2-carboxylic acid; acetylshikonin; actamycin; actinorhodin; aklanonic acid; alizarin; alizarin 1-methyl ether; alizarin complexone; aloe-emodin dianthrone diglucoside; aloesaponarin; aloin mixt. with phenolphtalein; alterporriol A; alterporriol B; alterporriol D; alterporriol E; altersolanol A; angelmicin A; angelmicin B; anthraquinone 1-sulfonate; anthraquinone; sulfonate; anthraquinone violet; aquayamycin; averantin; averufanin; averufin; barleriaquinone I; benzanthrin A; benzanthrin B; bostrycin; bromamine acid; butylmaduramycin; capoamycin; carmine; carminic acid; mucicarmine; osmium carmine; Cascara; Emodin; cascaroside; christofin; chrysophanic acid; chrysophanol dimethyl ether; cyanine green G base; D & C green 5; dactylariol; damnacanthal; danthron; DC92-B; DC92-D; deoxydynemicin A; diacetylrhein; digiferruginol; digitolutein; digitopurpone; dioxamycin; Disperse Blue 1; disperse blue 35; disperse red 9; dithianone; dothistromin; doxidan; DP; 110095; Drimarene brilliant blue; dynemicin A; dynemicin H; dynemicin M; dynemicin O; dynemicin P; dynemicin Q; dynemicin S; ekatetrone; elloramycin; flavoskyrin; frangulin B; fujianmycin A; fujianmycin B; funiculosin (anthraquinone); glutaryl-2-(hydroxymethyl)anthraquinone; grincamycin; hatomarubigin A; hatomarubigin B; hatomarubigin C; hatomarubigin D; hedamycin; isopinnatal; K 259-2; K 259-3; kerriamycin A; kerriamycin B; kerriamycin C; knoxiadin; KS 619-1; leiocarpaquinone; LHRH, lysine(6)-glutaryl-2-(hydroxymethyl)anthraquinone; losoxantrone; lucidin; lucidin; 3-O-beta-primveroside; lucidin ethyl ether; macrosporin; Mitoxantrone; 1,4-dihydroxy-5,8-bis((2-(2-hydroxyethoxy)ethyl)amino)-9,10-anthracenedione; 1-hydroxy-5,8-bis(2-((2-hydroxyethyl)amino)ethylamino)-9,10-anthracenedione; 4-(glycyl-histidyl-lysine)-1,5,8-trihydroxyanthraquinone; 4-(glycyl-histidyl-lysine)-1-hydroxyanthraquinone; 8,11-dihydroxy-4-(2-hydroxyethyl)-6-((2-((2-hydroxyethyl)amino)ethyl)amino)-1,2,3,4,7,12-hexahydronaphtho(2,3-f)quinoxaline-7,12-dione; ametantrone; aminatrone 1; BBR 2577; CL 232468; mitoxantrone carboxylic acid; mitoxantrone dicarboxylic acid; MM 47755; morindaparvin A; morindaparvin B; MT-81 toxin; N,N'-1,5-anthraquinonylenebisbenzamide; norsolorinic acid; NSC 639366; NU-ICRF 505; OM 4842; oxanthromicin; oxantrazole; PD 116779; physcion diglucoside; poly R-478; polycyanine; pyralvex berna; rabelomycin; Remazol Brilliant Blue R; remazol brilliant; blue R vinyl sulfone; rhein; rheochrysin; rhynchotechol; RMI 10024; RMI 9576DA; ruberythric acid; rubiadin; rubiadin 1-methyl ether; rubiginone; B1; rubrocristin; rufigallol; rugulosin; saquayamycin; saquayamycin B; saquayamycin C; saquayamycin D; sennoside A&B; sennoside C; sennoside E; serirubicin; SF 2330; skyrin; SM 196A; SM 196B; subspinosin; Synten; Brown; teloxantrone; thermorubin; triacetyidynemicin A; uniblue A; versicolorin A; versicolorin A; hemiacetal; versicolorin; versicolorins; versiconal; versiconal hemiacetal acetate; versiconol; versiconol; acetate; vineomycin A1; vineomycin A2; vineomycin B1; vineomycin B2; WS 009A; WS 009B; X-prep; 1,2-naphthoquinone; 1,2-naphthoquinone thiosemicarbazone; 1,2-naphthoquinone-4-sulfonate; 1,4-naphthoquinone; 1,4-naphthoquinone-2-sulfonate; 2,3-(di-glutathion-S-yl)-1,4-naphthoquinone; 2,3-bis(2-hydroxyethylsulfanyl)-(1,4)naphthoquinone; 2,3-bis(chloromethyl)-1,4-naphthoquinone; 2,3-dichloro-5,8-dihydroxy-1,4-naphthoquinone; 2,3-dimethoxy-1,4-naphthoquinone; 2,3-dimethyl-1,4-naphthoquinone; 2,5-diamino-1,4-naphthoquinone imine; 2-(4-methyl-5-isoxazolylamine)-N-(4-methyl-5-isoxazolyl)-1,4-naphthoquinone-4-imine; 2-amino-1,4-naphthoquinone imine; 2-aziridinyl-1,4-naphthoquinon-5-yl 4-ethylbenzenesulfonate; 2-aziridinyl-1,4-naphthoquinon-5-yl 4-tert-butylbenzenesulfonate; 2-aziridinyl-5-hydroxy-1,4-naphthoquinone; 2-chloro-1,4-naphthoquinone; 2-chloro-3-amino-1,4-naphthoquinone; 2-chloromethyl-1,4-naphthoquinone; 2-dimethylamino-3-chloro-1,4-naphthoquinone; 2-ethyleneimino-5,6,7,8-tetrahydronaphthoquinone; 2-hydroxy-1,4-naphthoquinone monothiosemicarbazone; 2-hydroxy-3-methyl-1,4-naphthoquinone monosemicarbazone; 2-hydroxy-3-n-dodecylmercapto-1,4-naphthoquinone; 2-hydroxy-3-undecyl-1,4-naphthoquinone; 2-hydroxyamino-1,4-naphthoquinone; 2-hydroxyjuglone; 2-methoxy-1,4-naphthoquinone; 2-methoxymethyl-1,4-naphthoquinone; 2-methyl-3-(N-acetylcystein-S-yl)-1,4-naphthoquinone; 2-methylthio-1,4-naphthoquinone; 298C80; 3,3'-biplumbagin; 3-(2-(dimethylamino)ethoxy)-1-hydroxybenzo(b)naphtho(2,3-d)furan-6,11-dione; 3-(glutathion-S-yl)-1,4-naphthoquinone; 3-allyl-beta-lapachone; 4-(cyclohexylmethylamino)-1,2-naphthoquinone; 5-(N-carbobenzyloxyamino)-1,4-naphthoquinone; 5-deoxyanhydrofusarubin; 5-deoxyfusarubin; 6-chloro-2,3-dihydroxy-1,4-naphthoquinone; 6-O-demethyl-5-deoxyanhydrofusarubin; 6-O-demethyl-5-deoxyfusarubin; 8,8'-biplumbagin; 8-methoxygriseorhodin C; A 80915A; aethiopinone; altromycin F; altromycin G; altromycin H; altromycin 1, AM 8402; arizonin A1; arizonin B1; arnebinone; atovaquone; aurofusarin; Basic Blue 99; beta, beta-imethylacrylshikonin; beta-hydroxyisovalerylshikonin; beta-lapachone; bonafton; buparvaquone; BW 58C; CGS 20111; chimaphilin; crisamicin A; crisamicin B; crisamicin C; cryptosporin; cycloalkannin; cycloalkannin leucoacetate; cypripedin; decalin-1,4-dione; deoxyfrenolicin; deoxylapachol; deoxyshikonin; diastovaricins I; diastovaricins II; dichlone; dichloroallyl lawsone; dihydrogranaticin; diospyrin; diosquinone; dunnione; echinochrome A; exfoliamycin; fibrostatin C; flaviolin; floccosin; frenolicin B; furaquinocin C; furaquinocin D; furaquinocin E; furaquinocin F; furaquinocin G; furaquinocin H; granaticin; griseusin; gunacin; herbarin; hydrolapachol; hydroxydihydrofusarubin; isodiospyrin; juglomycin; juglomycin Z; juglone; juglorin; kalafungin; lactoquinomycin A; lactoquinomycin B; lapachol; lawsone; luteoskyrin; luteosporin; M 92; mansonone A; MDS 004; mederrhodin A; mederrhodin B; menoctone; menoxymycin A; menoxymycin B; methyl 2-((3,4-dihydro-3,4-dioxo-1-naphthalenyl)amino)benzoate; methylspinazarin; misakimycin; mollisin; N-(3,4-dimethyl-5-isoxazolyl)-4-amino-1,2-naphthoquinone; naflocort; naftazone; nanaomycin A; nanaomycin B; nanaomycin C; nanaomycin E; naphterpin; naphthazarin; naphthgeranine A; naphthgeranine B; naphthgeranine C; naphthgeranine D; naphthgeranine E; naphtho(1,2-b)furan-4,5-dione; naphtho(2,3-b)furan-4,9-dione; naphthomevalin; naphthomycin; naphthopyranomycin; naphthoquinomycin A; naphthoquinomycin B; napyradiomycin A1; napyradiomycin A2; napyradiomycin B1; napyradiomycin B4; napyradiomycin C1; napyradiomycin C2; nickel lapachol; O-ethylfusarubin O-ethylhydroxydihydrofusarubin; OM 173; parvaquone; phthiocol; plastatin; plumbagin; protorubradirin; psychorubrin; purpuromycin; rhinacanthone; rubradirin; rubradirin aglycone; rubradirin B; rubransarols; rugulin; salvicine; sapriparaquinone; sarubicin B; shikonin; spinochrome A; stahlianthusone; thermoplasmaquinone; tricrozarin A; tricrozarin B; ventilagolin; viomellein; Vitamin K 1; 2-(3,7,11,15,19,23-hexamethyl-25-(2,6,6-trimethylcyclohex-2-enyl)pentacosa-2,14,18,22-tetraenyl)-3-methyl-1,4-naphthoquinone; 2-(fluoromethyl)-3-(phytyl)-1,4-naphthoquione 2,3-epoxide; 2-(fluoromethyl)-3-phytyl-1,4-naphthoquinone; 2-trifluoromethyl-3-phytyl-1,4-naphthoquinone; 3-hydroxy-2-methyl-3-phytyl-2,3-dihydronaphthoquinone; chloro-K; gamma-hydroxyvitamin K; vitamin K semiquinone radical; vitamin K-1 epoxide-1,4-diol; vitamin K1 aglycone I; vitamin K1 aglycone II; vitamin K1 aglycone III; vitamin K1 chromenol; vitamin K1 hydroquinone; vitamin K1 oxide; vitamin K1-hydroperoxide; Vitamin K2; 2-trifluoromethyl-3-geranyl-1,4-naphthoquinone; demethylmenaquinone; menadione dimethylpyrimidinol bisulfite; menahydroquinone-4; menaquinone 6; menaquinone 9; menatetrenone; tetrahydromenaquinone; vitamin MK 7; vitamin MK 8; Vitamin K 3; 3-bromomethyl-menadione; astato-2-methyl-1,4-naphthoquinol diphosphate; menadione epoxide; menadione nicotinamide bisulfite; menadione semiquinone; vitamin k5; WS-5995 B; xanthomegnin; xyloidone, or any combinations thereof.

In a particularly preferred embodiment, the compounds of the invention are used at a sub MIC concentration. The term MIC (Minimal Inhibitory Concentration) as used herein is defined as the lowest concentration of drug that marks the inhibition of growth on a absorbance-concentration plot.

In another preferred embodiment, the above-mentioned compounds are applied at a concentration at which they are not bactericidal. Preferably, the present compounds are applied at a final concentration, at which they are not bactericidal. The term "final concentration" refers to the total concentration of the compound(s) in the end product. The end product may include the pure compound(s) as such, or an extract, extract fraction, composition or an oral/food/or drink product as defined herein.

Extract

The present invention also relates to the use of a plant extract or active fraction thereof which comprises a compound according to the invention to prevent and/or inhibit the formation of biofilm, preferably in the oral cavity. The present invention also relates to the use of a plant extract or active fraction thereof which comprises a compound according to the invention to treat a biofilm, preferably in the oral cavity. In another embodiment, the invention relates to a plant extract or active fraction thereof which comprises a compound according to the invention for preventing and/or treating dental plaque formation and thereto related diseases.

The present invention particularly provides a plant extract which is obtained from one or more plants selected from the group comprising *Acacia* sp., *Agnus* sp., *Aloe* sp., *Alium* sp., *Amygdalus* sp., *Azadirachta* sp., *Angelica* sp. *Barosma* sp., *Cassia* sp., *Centella* sp., *Cerasus* sp., *Ceratonia* sp., *Chamomilla* sp., *Chimaphila* sp., *China rubra* sp., *Cinnamomum* sp., *Citrus* sp., *Cochlearia* sp., *Jateorhiza* sp., *Eugenia* sp., *Fagopyrum* sp., *Panax* sp., *Haematoxylum* sp., *Hammamelis* sp., *Hypericum* sp., *Juglans* sp., *Lavendula* sp., *Lycopus* sp., *Mentha* sp., *Myrtus* sp., *Oenothea* sp., *Origanum* sp., *Phyllantes* sp., *Podophylum* sp., *Polygonatum* sp., *Polygonum* sp., *Prunus* sp., *Punica* sp., *Rhamnus* sp., *Rheum* sp., *Rubus* sp., *Rumex* sp., *Salvadora* sp., *Simarouba* sp., *Solanum* sp., *Sorbus* sp., *Terrminalia* sp., *Thymus* sp., *Uva-ursi* sp., *Vitis* sp., *Woodfordia* sp., *Zea* sp., or any combinations hereof. These plant extracts are in particular characterized in that they have a pharmacological activity and in particular a biofilm inhibitory activity.

Extracts according to the present invention have a biofilm inhibitory activity and show the particular advantage of being active at non-bactericidal concentrations. Extracts of above-mentioned plants thus inhibit the formation of a biofilm, preferably a dental biofilm, at certain concentrations without being bactericidal. The above-mentioned extracts have the particular advantage to inhibit biofilm formation by reducing EPS, and the bacterial colonies in the biofilm or by damaging the cellular integrity of the bacteria without being bactericidal as such. This feature is of major importance to limit bacterial resistance.

More particularly, extracts of above-mentioned plants may show a GTF inhibiting activity, and/or the ability to reduce biofilm formation by means of an activity that differs from GTF inhibition. In one embodiment the invention therefore provides an extract according to the present invention, characterized in that this extract has a pharmacological activity, and particularly an anti-GTF activity. In another embodiment the invention provides an extract, according to the present invention, characterized in that this extract has a pharmacological activity, and a biofilm inhibitory activity that differs from an anti-GTF activity.

In a preferred embodiment the invention relates to a plant extract which is obtained from one or more plants selected from the group comprising *Acacia* sp., *Agnus* sp., *Amygdalus* sp., *Azadirachta* sp., *Citrus* sp., *Jateorhiza* sp., *Eugenia* sp., *Haematoxylum* sp., *Hypericum* sp., *Juglans* sp., *Myrtus* sp., *Oenothea* sp., *Prunus* sp., *Punica* sp., *Rheum* sp., *Rubus* sp., *Rumex* sp., *Salvadora* sp., *Solanum* sp., *Terminalia* sp., *Uva-ursi* sp., *Woodfordia* sp., *Zea* sp., or combinations hereof. These extracts were identified as particularly capable of efficiently inhibiting the glucosyl transferase enzyme.

In another preferred embodiment the present invention relates to a plant extract which is obtained from one or more plants selected from the group comprising *Acacia* sp., *Amygdalus* sp., *Cerasus* sp., *Ceratonia* sp., *Chimaphila* sp., *China rubra* sp., *Eugenia* sp., *Haematoxylum* sp., *Hammamelis* sp., *Hypericum* sp., *Juglans* sp., *Lycopus* sp., *Myrtus* sp., *Oenothea* sp., *Podophylum* sp., *Polygonum* sp., *Prunus* sp., *Punica* sp., *Rheum* sp., *Rubus* sp., *Terminalia* sp., *Uva-ursi* sp., *Vitis* sp., or any combinations hereof. These extracts were identified as particularly capable to inhibit biofilm formation. Moreover these plant extracts show an inhibitory effect on dental biofilm formation which is at least partially different from an anti-GTF effect.

In still another preferred embodiment the present invention relates to a plant extract which is obtained from one or more plants selected from the group comprising *Acacia* sp., *Amygdalus* sp., *Eugenia* sp., *Haematoxylum* sp., *Hypericum* sp., *Juglans* sp., *Myrtus* sp., *Oenothea* sp., *Prunus* sp., *Punica* sp., *Rheum* sp., *Rubus* sp., *Terrminalia* sp., *Uva-ursi* sp., *Woodfordia* sp. or any combinations hereof. Above-mentioned extracts were identified as particularly capable to inhibit dental biofilm formation. The most important activities of these extracts are an anti-GTF activity and an inhibitory effect on biofilm formation, e.g. on the dental surface, by an activity different from an anti-GTF activity.

In a preferred embodiment the invention provides a plant extract which is obtained from one or more plants selected from the group comprising *Chimaphila* sp., *Eugenia* sp., *Haematoxylum* sp., *Hammamelis* sp., *Myrtus* sp., *Prunus* sp., *Punica* sp., *Rheum* sp., *Uva-ursi* sp., *Woodfordia* sp. or any combinations thereof.

In another embodiment the invention provides the use of a plant extract which is obtained from one or more plants selected from the group comprising *Cassia angustifolia, C. senna.* (*senna*), *C. fistula, Rhamnus frangula, R. catharticus, R. purshianus, Aloe vera* and *A. ferox* or any combinations thereof, to prevent and/or inhibit biofilm formation, preferably of an oral biofilm.

In a particularly preferred embodiment the invention relates to the use of an extract of a *Rheum* sp., and preferably *Rheum palmatum, Rheum rabarbarum* and/or *Rheum raponthicum*, to prevent and/or inhibit biofilm formation, preferably to prevent and/or inhibit oral biofilm formation.

In a further preferred embodiment the invention provides an extract consisting of a combination of different plant extracts or fractions thereof, such as preferably a combination of extracts and fractions thereof of *Rheum* sp., *Prunus* sp., *Myrtus* sp. *en Punica* sp. An extract consisting of a combination of different plant extracts has the advantage of showing a higher biofilm inhibitory activity than an extract isolated out of one plant. In still another preferred embodiment the invention provides an extract or fractions thereof obtained from one or more of the above-mentioned plants, and a green tea extract. An extract consisting of a combination of different plant extracts or fractions hereof, in combination with a green tea extract, has the advantage of showing a higher biofilm inhibiting activity than a green tea extract as such.

Surprisingly the extract according to the invention has a significant higher biofilm inhibitory activity than green tea. Moreover, the extract according to the present invention has the particular advantage to show a very strong biofilm inhibitory activity at relative low doses. More particularly extracts, tested at concentrations below a bactericidal value (MIC value), already show a particularly good biofilm inhibitory effect. An extract according to the invention shows a good biofilm inhibitory activity at doses in the range of 100-500 µg and preferably in the range of 150-390 µg dry dust particles per ml sugar and nutrient containing irrigation medium (e.g. BHIS: Brain Heart infusion+sugar).

The extract according to the present invention can comprise a non-purified as well as a purified and/or concentrated extract. The extracts according to the invention preferably are concentrated preparations of liquid, solid or intermediate consistence derived from vegetable material. The extract according to the present invention shows no bactericidal action at the used concentrations.

An extract according to the present invention preferably is an extract of a fruit, a root, a bark, a branch, a leaf, a seed, a stalk, a tuber, a bulb, a flower, and/or parts of this and/or mixtures. Plant parts which can be used to prepare an extract according to the present invention, comprise but are not limited to fruits (fructus), leafs (folium), seed fruits (fructus s. semen), roots (radix), barks (cortex), branches, blossoming branches, seed (semen), rootstocks (rhizoma), root and herb (radix cum herba), stalks, the whole plant, herb (herba), tuber (tuber), bulb (bulbus), pericarpium, stramentum, flowers (flos), leafs and bloom (folium cum flores), stipites, stigma, lignum, strobulus, thallus, gums (gummi), lichenes, aboveground parts, blossoming aboveground parts, underground parts. These plant parts can be fresh, dried or frozen.

In an embodiment the starting material or an intermediate product for some preparations needs to undergo a pre-treatment like for example, but not limited to, the inactivation of enzymes, oxidation, hydrolysis, heating, grinding or degreasing.

Examples of solvents which are useful in extracting abovementioned plants comprise water or preferred mixtures of water and one or more polar solvents as lower alcohols, e.g. methanol and ethylalcohol, acetone but also supercritical gases such as carbon dioxide, nitrogen or other inert gases. Among these solvents liquid at atmospheric pressure, the use of water, ethylalcohol or a mixture thereof is preferred in view of the fact that the extract could be used in oral preparations and/or food. Among the gaseous solvents that are liquefied at high pressure, supercritical $CO_2$ is preferred for the same reason. The ratio of solvent to the plant parts to extract is not limited, but preferably the solvent is applied in a 2- to 1000-fold higher amount and preferably 20- to 100-fold higher in mass percentage than the amount of plant parts to extract. The extraction temperature can easily be chosen in the range of room temperature to the boiling point of the solvent under the desired pressure. The extraction time can preferably range from 10 minutes to some days and can vary depending on the extraction temperature. The extraction pressure is to be diligently chosen in function of temperature and time. In a preferred embodiment the invention provides a plant extract, whereby the solvent used for the extraction is selected out of the group containing water, ethanol, propylene glycol, glycerine, methanol, acetone, methylene chloride, ethylene chloride, vegetable oils, supercritical gases such as $CO_2$, an acid and/or base in pure form and/or mixtures of these.

The starting material to be extracted may be previously reduced, if necessary, to pieces of a desired size. This plant material is then thoroughly mixed with a part of the extraction solvent after which the mixture is stored during a specific time for better maceration. In case of liquid extraction, the residue is separated from the extraction solvent or the mixture is further transferred to a percolator where it is being percolated at low speed, whereby the extracting material preferably remains covered by the residual extraction solvent. The residue can be squeezed and the squeezed liquid can be merged to the earlier derived liquid. Other extraction methods like the counter-current extraction can also be applied. In case of supercritical extraction, the effluent gas dissipates leaving a liquid extract and a spent residue which both are dried at the air or by heating.

Concentration to obtain a desired consistency is done by an appropriate method such as evaporation under reduced pressure and at a temperature whereby degradation of the components is minimally reduced, or by freeze-drying, or by evaporation, or by nebulisation or another method. Standardized extracts are brought to the desired content of components for example by addition of appropriate inert materials or by use of another extract of the plant.

In a further embodiment the invention also relates to one or more active fractions of above-mentioned extract. As mentioned above, the term "active fraction" herein relates to a part of the extract obtained by a fractionation procedure and having an activity similar to one or more activity(ies) of the extract(s) namely a biofilm inhibitory action and/or an anti-GTF activity and/or an additional activity. This fraction can comprise a polar fraction, an apolar fraction, or combinations hereof, etc. Examples of these are discussed in example 6. Fractionation techniques are well-known by an expert and are not discussed here in detail.

In a preferred embodiment the present invention relates to the use of an extract as herein defined, in which an active extract fraction comprises a polar and/or apolar fraction or combination hereof. In an embodiment the present invention provides the use of a(n) (a)polar extract fraction as herein defined as biofilm inhibitor or as GTF inhibitor. In a preferred embodiment the present invention provides the use of an apolar extract fraction as herein defined as biofilm inhibitor. In another preferred embodiment the present invention provides the use of a polar extract fraction as herein defined as GTF inhibitor.

In still a further embodiment the invention relates to one or more active compounds isolated out of an extract or an extract fraction of one or more of above-mentioned plants. As explained above, the term "active compound" herein refers to a component present in a plant extract or a fraction having an activity similar or superior to at least one of the extract's activities. The extract according to the invention may consist of one or more active compounds, showing at least one of the extract's activities. The most important activities of the extract are an anti-GTF activity and/or a biofilm inhibitory effect by an activity different from an anti-GTF activity. An active compound may show at least one, or even both effects or also other additional effects.

In a particularly preferred embodiment the present invention provides the use of one or more active compounds, or of one or more extracts or active fractions thereof, as defined herein, whereby the active compounds may be selected out of the group containing quinones as naphtoquinones, anthraquinones, hydroxyl-anthraquinones, dianthrones, anthranol and macrocyclic naphtodianthrones; but also phenylbutanones, polyphenoles as flavonoides, flavonols, flavones, flavanones, catechins, anthocyans, isoflavonoides, tannins, elagotannins, etc. . . . . .

Composition

In another aspect, the invention relates to a composition for preventing and/or inhibiting the formation of a biofilm, which comprises an effective amount of at least one compound and/or of a plant extract or active fraction thereof comprising said compound, as defined herein. The invention preferably relates to a composition for preventing and/or inhibiting the formation of a biofilm, which comprises an effective amount of at least one compound selected from the group comprising an anthraquinone and a naphtoquinone, stereoisomeric forms, racemic mixtures, metabolites, esters or salts thereof, or mixtures thereof, and/or of a plant extract or active fraction thereof comprising said compound, as defined herein. The invention also relates to a composition for treating a biofilm, which comprises an effective amount of at least one compound selected from the group comprising an anthraquinone and a naphtoquinone, stereoisomeric forms, racemic mixtures, metabolites, esters or salts thereof, or mixtures thereof, and/or of a plant extract or active fraction thereof comprising said compound, as defined herein. The herein presented compositions are suitable for preventing and/or inhibiting the formation of any type of biofilm, or for treating a biofilm, and in particularly suitable for preventing and/or inhibiting the formation of a biofilm in the oral cavity or for treating a biofilm in the oral cavity.

In another embodiment, the invention provides a composition for preventing and/or inhibiting the formation of a biofilm, or for treating a biofilm, comprising a polar extract fraction and an apolar extract fraction of at least two plants, whereby said plants may be the same or different and selected from the group as defined herein, for simultaneous, separate or sequential use. Preferably, said apolar extract fraction contains at least one active compound as defined herein.

In a preferred embodiment, the invention provides a composition comprising a polar extract fraction and an apolar extract fraction of at least two plants, whereby these plants can be similar or different and are selected from the group comprising *Acacia* sp., *Agnus* sp., *Aloe* sp., *Alium* sp., *Amygdalus* sp., *Azadirachta* sp., *Angelica* sp. *Barosma* sp., *Cassia* sp., *Centella* sp., *Cerasus* sp., *Ceratonia* sp., *Chamomilla* sp., *Chimaphila* sp., *China rubra* sp., *Cinnamomum* sp., *Citrus* sp., *Cochlearia* sp., *Jateorhiza* sp., *Eugenia* sp., *Fagopyrum* sp., *Panax* sp., *Haematoxylum* sp., *Hammamelis* sp., *Hypericum* sp., *Juglans* sp., *Lavendula* sp., *Lycopus* sp., *Mentha* sp., *Myrtus* sp., *Oenothea* sp., *Origanum* sp., *Phyllantes* sp., *Podophylum* sp., *Polygonatum* sp., *Polygonum* sp., *Prunus* sp., *Punica* sp., *Rhamnus* sp., *Rheum* sp., *Rubus* sp., *Rumex* sp., *Salvadora* sp., *Simarouba* sp., *Solanum* sp., *Sorbus* sp., *Terrminalia* sp., *Thymus* sp., *Uva-ursi* sp., *Vitis* sp., *Woodfordia* sp., *Zea* sp. for separate, sequential, or simultaneous use to treat biofilms, and preferably out of the group comprising *Acacia* sp., *Amygdalus* sp., *Eugenia* sp., *Haematoxylum* sp., *Hypericum* sp., *Juglans* sp., *Myrtus* sp., *Oenothea* sp., *Prunus* sp., *Punica* sp., *Rheum* sp., *Rubus* sp., *Terrminalia* sp., *Uva-ursi* sp., *Woodfordia* sp. or any combinations hereof, and more preferably out of the group comprising *Punica* sp., *Myrtus* sp., *Hypericum* sp. and *Rheum* sp.

Preferably compositions are provided whereby at least one polar extract fraction of *Rheum* or at least one apolar extract fraction of *Rheum* are applied, optional in combination with polar and/or apolar extract fraction(s) of one or more other plant(s), such as those herein defined. In another example, compositions can be provided whereby at least a polar extract fraction of *Rheum* is applied optionally in combination with polar and/or apolar extract fraction(s) of one or more other plant(s), as defined herein. In still another example compositions can be provided whereby at least one apolar extract fraction of *Rheum* is applied optionally in combination with polar and/or apolar extract fraction(s) of one or more other plant(s), as defined herein.

In another embodiment, the invention provides a composition for preventing and/or inhibiting the formation of a biofilm, or for treating a biofilm, comprising:
  an effective amount of an extract, or an active compound, or an active fraction thereof as defined herein, and
  at least one polar extract fraction of a plant selected from the group as defined in herein, for simultaneous, separate or sequential use.

Preferably, said polar extract fraction contains provides an anti-GTF effect.

In a further embodiment the invention provides a composition comprising an effective amount of an extract, or an active compound, or an active (a)polar fraction, as herein defined, optionally in combination with an appropriate filling agent, for the treatment and/or prevention of dental plaque, dental tartar, and/or thereto related dental diseases. The term "effective amount" refers to that amount of active compound(s) that activate(s) the biological or medical response in a tissue, system, animal or man, which is intended by a researcher, veterinary surgeon, dentist or doctor, and which contains reducing the symptoms of that disease or disease that is treated. The effective amount depends on the disease to treat and the professional skills of the therapist.

In another embodiment, the invention provides a composition as defined herein which further comprising an effective amount of at least one other component that is adapted to prevent and/or inhibit the formation of dental plaque and/or dental tartar. The composition may thus comprise:

an effective amount of an extract, or an active compound, or an active fraction thereof as defined herein, and an effective amount of at least one other component that is appropriate to prevent and/or inhibit the formation of dental plaque and/or dental tartar formation, possibly in combination with an appropriate filling agent.

Such composition is preferably a combined preparation for simultaneous, combined, separate or combined use for the treatment of dental tartar formation and/or dental plaque. A component to prevent or treat or inhibit the formation of dental tartar comprises for example a component selected from of the group comprising pyrophosphates, polyphosphates, phosphonates, zinc citrate, etc. . . . . . A component to prevent or treat or inhibit the formation of dental plaque comprises for example a component selected from of the group containing fluoride (sodium fluoride, sodium monofluorphosphate, tinfluoride, aminofluoride); chlorehexidine, sanguinarine, triclosan, etc. . . . . . It shall be clear that the compositions according to the present invention are not a mere complex of known components, but a new combination, which shows a surprising and valuable effect, i.e. improved effects on the treatment of dental plaque combined with improved effects on the treatment of dental tartar formation. Better, synergistic effects are obtained when using the present combined compositions provide, than when using its components as such.

The amount of an extract and/or an active fraction(s) and/or (an) active compound(s) thereof in a composition, as defined herein, preferably ranges from 0.01 and 90% w/v; and for example from 1.0 to 35% w/v, or for example from 1.5 to 25% w/v, or for example from 2.0 to 10% w/v.

The present compositions can be prepared easily by a person of skill in the art. One or more of the present extracts, active compounds, and/or active fractions thereof according to the invention are brought together in an appropriate administration form or dosage form after which the composition can be used as a drug, food or cosmetic product for animal or human use. A composition with one or more extracts, active compounds, or active fractions according to the invention can be prepared according to routine methods by mixing an effective amount of active ingredient with several pharmaceutical ingredients appropriate for the definitive administration from, like organic or inorganic carriers, filling agents, binding agents, wetting agents, disintegrators, lubricants and diluents and other additives, e.g. additives appropriate for oral use.

In a preferred embodiment one or more of the extracts, active compounds, or active fractions according to the invention are appropriate for oral administration. The extracts, active compounds, or active fractions for oral administration according to the invention can be prepared for example in a solid oral dosage form or in a liquid dosage form according to routine methods by applying organic and/or inorganic carriers, filling agents, or other additives appropriate for oral administration.

Solid oral dosage forms may comprise tablets, powders, small particles, grains, capsules, pills and dispersion forms, and the like. For veterinary applications, solid oral dosage forms may also include dental chews, chewing bones, petfood products, treats, chew strips, and all kinds of biting contraptions and biting toys from either edible or non-edible material. These dental chew forms may be obtained by various routine processes such as extrusion, injection, pressing and demoulding, etc. . . . . . In all these dosage forms, one or more of the extracts, active compounds, or active fractions according to the invention are mixed with at least one inactive diluent, for example lactose, mannitol, glucose, cellulose, starch, maize starch, polyvinylpyrrolidone, etc. According to routine methods, besides inactive diluents the composition can contain, as desired, other additives, for example binding agents like hydroxypropyl cellulose and hydroxypropylmethyl cellulose (HPMC); lubricants like magnesium stearate, polyethylene glycol, starch en talc; disintegrators like glycolate of fibrinogene calcium; stabilizing agents like lactose; dissolution agents like glutamic acid or aspartic acid; plasticizing agents like polyethylene glycol; coloring agents like titan oxide, talc and iron oxide. If necessary, the resulting tablet or pill can be covered, as desired, with a covering sugar layer or film composed of substances soluble in stomach or intestine, like sucrose, gelatine, agar, pectine, hydroxypropyl cellulose, etc. The oral dosage form preferably comprises a stabile and robust dosage form, easy for the patients to absorb and appropriate for storage and transport.

Liquid oral dosage forms can comprise emulsions, solutions, suspensions, syrups, mouthwash liquids or elixirs and contain inactive diluents for general use, for example distilled water and ethylalcohol. Besides inactive diluents, the composition also can comprise components like wetting agents, suspending components, sweeteners, aromas, odors and preservatives.

The compositions according to this invention can be administered to humans or animals in dose ranges specific for each of the components in the compositions. It goes without saying that dosage levels and administration frequencies specific for any patient can be adapted and will depend on several factors including the activity of the specific applied component(s), the metabolic stability and the operation period of the composition, the composition, the age, the body weight, the general health, the gender, the diet, the method and time of the administration, the excretion level, the seriousness of the disease and the person who undergoes the therapy.

Products

In a further embodiment the invention relates to an oral health product for preventing and/or inhibiting the formation of a biofilm comprising one or more compounds, or of a plant extract or active fraction thereof comprising said compound as defined herein, or composition as defined herein. In a preferred further embodiment the invention relates to an oral health product for preventing and/or inhibiting the formation of a biofilm comprising one or more compounds selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein, or composition as defined herein.

In another further embodiment the invention relates to an oral health product for treating a biofilm comprising one or more compounds selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein, or composition as defined herein.

The term "oral health product" as applied herein refers to a product applied for the maintenance of oral hygiene. The present oral product may be suitable for human or animal use. The oral health product comprises an extract like defined above. It goes without saying that this product may comprise one or more plant extracts whereby all possible combinations of extracts are possible. The oral health product can also comprise an active compound an active fraction as defined herein, or all possible combinations hereof. Non limiting examples of such products comprise a gel, a paste, a gum, a stick pill, a rinsing liquid, a toothpaste, a strip, a chew, a tablet, soluble tablet or similar, a topical medicament, an oral dentifrice, an injectable composition, an oral tablet, a lozenge or a soft gelatin capsule, a rinsing agent, a dispersing solution, a chewing gum, an ointment, a solution, a powder and the like.

For animal use, for example for dogs or cats, specific oral health products may be provided, like for example chewing rods or bones, a chewing strip, a specific (tooth)paste or gel, and the like.

In an example, a veterinary product may be developed and consist of a chewing bone comprising 50%-85% by weight of cereal flour such as from rice, corn (maize), wheat, rye, sorghum, millet, etc. . . . 5-10% by weight of cereal gluten (again from the said selection of cereals), 0-10% by weight of animal bye-products, 2.5-7.5% by weight of a humectant such as glycerin, 1-2% by weight of vegetal oil, 1-3% by weight of (di, tri) calcium phosphates and 0.2-0.5% by weight potassium sorbate. Such and other chewing bone may serve as pharmaceutical vehicle for inclusion of the compound(s), fraction(s) and extract(s) as defined above.

In addition to the above mentioned extract(s), active compound(s), and/or an active extract fraction(s) as defined above, oral health products preferably may further comprise a number of additives including water, binding agents, cleaners and abrasives, absorbing agents, flavoring and coloring agents aromas, sweeteners, solvents for oils, preservatives, dental tartar inhibitors, vitamins, plaque inhibitors, fluorides. Examples of additives comprise among others calcium carbonate, calcium hydrogen phosphate, silicic acid, magnesium carbonate, glycerine, sorbitol, propylene glycol, polyethylene glycol, carboxymethyl cellulose, methyl cellulose, sodium alginate caragene, carboxylvinyl polymer, sodium dioctylsulfosuccinate, sodium laurylsulfate, sodium dodecylbenzenesulfonate, butyl paraoxybenzoate, hinokitiol, allantoin, glytyiricin, alcohol, arabic gum, starch, mais starch, sodium sacharinate, stevioside, glucose, lactose, magnesiumstearate, monopotassium phosphate, dipotassium phosphate, menthol, eucalyptus oil, peppermint, green pepper, and pigment. Moreover, fluorides like sodium fluoride and sodium monofluorophosphate; anti inflammatory agents, like lypozymechloride and azulene; sodium chloride; or enzymes and their co-enzymes and substrates as lactoperoxidase, amyloglucoxidase and the like can also be added if desired.

In oral health products, agents such as fluoride, sodium fluoride, triclosan, chlorehexidine, etc., are usually added for prevention and treatment of dental plaque. These agents show an inhibitory effect against the development of oral bacteria. The effect of these agents usually tested on free-living bacteria. However, bacteria fixed in a biofilm usually show other phenotypes than free-living (planktonic) bacteria. Hence, antimicrobials developed against planktonic bacteria are not always effective against sedentary bacteria. The present invention now provides a composition and/or a herein provided compound, plant extract or active fraction thereof, that improves the efficacy of an oral health product. in addition to having an antimicrobial effect, such products will also affect dextran formation and virulence of the sedentary bacteria, growing in a biofilm, and thus be capable of inhibiting biofilm formation. Hence, the present composition and/or a herein provided compound, plant extract or active fraction thereof is a valuable and accurate additive for an oral health product for prevention and treatment of biofilm formation in general and of dental plaque and dental tartar, and dental diseases related thereto. Oral health products which contain known agent(s) against dental plaque and dental tartar as well as a composition and/or a herein provided compound, plant extract or active fraction thereof extract according to the present invention have a combined effect: such oral products inhibit EPS formation by biofilm forming micro-organisms and affects planktonic bacteria as well as sedentary bacteria, anchored. in a biofilm.

The present composition and/or a herein provided compound, plant extract or active fraction thereof already provides at sub-inhibitory concentrations an effect against a *S. mutans* biofilm superior to the activity of conventional concentrations of sodium fluoride, chlorehexidine and triclosan (FIG. 7) Hence, such an oral product will show a much more effective effect against dental plaque and dental tartar.

In yet another embodiment the invention relates to a food, feed or drink for preventing and/or inhibiting the formation of a biofilm, or for treating a biofilm in a person or an animal, and preferably but not limited to oral biofilms. The present invention also relates to a food, feed or drink for the treatment and/or prevention of dental plaque and dental tartar and/or dental diseases related thereto in a person or an animal. The invention relates to a food or feed or drink product for preventing and/or inhibiting the formation of a biofilm comprising one or more compounds, or of a plant extract or active fraction thereof comprising said compound as defined herein, or composition as defined herein. Preferably such food or feed or drink product for preventing and/or inhibiting the formation of a biofilm comprises one or more compounds selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein, or composition as defined herein.

For animal use, for example dogs or cats, specific food/feed or drinks, an extract(s), active compound(s) or (an) active fraction(s) as defined herein can be provided for treating biofilms, such as for example (hard) dog food, chewing rods or bones or strips, and the like.

The invention further relates to a veterinarian product for preventing and/or inhibiting the formation of a biofilm comprising one or more compounds, or of a plant extract or active fraction thereof comprising said compound as defined herein, or composition as defined herein. In yet another embodiment the invention relates to a veterinarian product for preventing and/or inhibiting the formation of a biofilm, or for treating a biofilm in a person or an animal, and preferably but not limited to oral biofilms, which comprises one or more compounds selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein, or composition as defined herein. Such veterinarian products may include but are not limited to chewing products obtained by techniques well known in the art such as for instance extrusion, injection, or molding of (non) edible chewable materials.

In another aspect, the invention further relates to a cosmetic product for preventing and/or inhibiting the formation of a biofilm comprising one or more compounds, or of a plant extract or active fraction thereof comprising said compound as defined herein, or composition as defined herein. Preferably, the present invention provides for a cosmetic product for preventing and/or inhibiting the formation of a biofilm, or for treating a biofilm which comprises an effective amount of at least one compound selected from the group comprising an anthraquinone and a naphtoquinone, stereoisomeric forms, racemic mixtures, metabolites, esters or salts thereof, or mixtures thereof, and/or of a plant extract or active fraction thereof comprising said compound, as defined herein. Cosmetic products may include but are not limited to skin care creams, products for cleaning and rinsing contact lenses, shampoos, conditioners, crème, ointments, products for hair care, make up, etc. . . . .

The amount of an extract(s) and/or of an active fraction(s) and/or of an active compound(s) as defined herein in an oral health product or in a food/feed or drink product or in a cosmetic product or a veterinarian product preferably ranges from 0.01 to 90% w/v; and for example from 0.5 to 70% w/v, and for example from 1.0 to 35% w/v, or from 1.5 to 25% w/v, or for example from 2.0 to 10% w/v.

Use—Methods

In a further aspect, the present invention provides the use at least one extract, or active compound, or active fraction, or composition, as defined above, for preventing and/or inhibiting the formation of a biofilm. In another further aspect, the present invention provides the use at least one extract, or active compound, or active fraction, or composition, as defined above, for treating a biofilm.

In a particular embodiment the invention relates to the use of an extract, or an active compound including naphtoquinones, anthraquinones, stereoisomeric forms, racemic mixtures, metabolites, esters or salts thereof, or mixtures thereof, or a polar or apolar extract fraction, or a composition as defined herein as a biofilm inhibitor and/or as a GTF inhibitor. In a preferred embodiment, the invention relates to the use of an extract, or an active compound thereof, or a polar extract fraction, or a composition as defined herein as a as a GTF inhibitor. In yet another preferred embodiment, the invention relates to the use of an extract, or an active compound thereof, or an apolar extract fraction, or a composition as defined herein as a as a biofilm inhibitor. In a particular embodiment the invention also relates to the use of an extract, or an active compound including phenylphenylbutanones, catechins and tannins thereof or a polar or apolar extract fraction, or a composition as defined herein as a biofilm inhibitor and/or as a GTF inhibitor.

In still another embodiment the invention relates to the use of an extract, or an active compound including naphtoquinones, anthraquinones, stereoisomeric forms, racemic mixtures, metabolites, esters or salts thereof, or mixtures thereof, or a polar or apolar extract fraction, or a composition as defined herein as an oral health product. In yet another particular embodiment the invention provides for the use of an extract, or an active compound as defined herein and including naphtoquinones, anthraquinones, stereoisomeric forms, racemic mixtures, metabolites, esters or salts thereof, or mixtures thereof, or a polar or apolar extract fraction, or a composition as defined herein as a food or a drink. In still another embodiment the invention relates to the use of an extract, or an active compound including phenylbutanones, catechins and tannins thereof or a polar or apolar extract fraction, or a composition as defined herein as an oral health product. In yet another particular embodiment the invention provides for the use of an extract, or an active compound including phenylbutanones, catechins and tannins thereof or of a polar or apolar extract fraction, or a composition as defined herein as a food or a drink.

In yet other embodiment, the invention relates to the use of an extract, or an active compound including naphtoquinones, anthraquinones, stereoisomeric forms, racemic mixtures, metabolites, esters or salts thereof, or mixtures thereof, as defined herein, or a polar or apolar extract fraction, or a composition as defined herein as a cosmetic product, or for the preparation of a cosmetic product. In another particular embodiment the invention provides for the use of an extract, or an active compound including phenylbutanones, catechins and tannins thereof or of a polar or apolar extract fraction, or a composition as defined herein as a cosmetic product.

In a further embodiment the invention relates to the use of an extract, or an active compound including naphtoquinones, anthraquinones, stereoisomeric forms, racemic mixtures, metabolites, esters or salts thereof, or mixtures thereof, as defined herein, or of a polar or apolar extract fraction, or a composition as defined herein as a medicament.

In a further embodiment the invention relates to the use of an extract, or an active compound including naphtoquinones, anthraquinones, stereoisomeric forms, racemic mixtures, metabolites, esters or salts thereof, or mixtures thereof, as defined herein, or of a polar or apolar extract fraction, or a composition as defined herein for the preparation of a medicament for preventing and/or inhibiting the formation of a biofilm. In another further embodiment the invention relates to the use of an extract, or an active compound including naphtoquinones, anthraquinones, stereoisomeric forms, racemic mixtures, metabolites, esters or salts thereof, or mixtures thereof, as defined herein, or of a polar or apolar extract fraction, or a composition as defined herein for the preparation of a medicament for treating a biofilm.

Preferably, the present medicament is in the form of a gel, a paste, a gum, a stick pill, a rinsing liquid, a toothpaste, a strip a tablet, soluble tablet or similar, a topical medicament, an oral dentifrice, an injectable composition, an oral tablet, a lozenge or a soft gelatin capsule.

In another embodiment, the invention relates to a method for preventing and/or inhibiting biofilm formation comprising administering an effective amount of one or more compounds selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein, or of a composition as defined herein. In yet another embodiment, the invention relates to a method for treating a biofilm comprising administering an effective amount of one or more compounds selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein, or of a composition as defined herein.

As previously mentioned, the term "biofilm" is to be encompassed in its broadest sense. The present invention thus provides a method of preventing or inhibiting the formation of any type of biofilm, or for treating a biofilm, including but not limited to biofilms which are formed on any type of surface, including the surface of teeth, human or animal cells, body parts or organs but also surfaces any type of medical devices such as tubes, catheters including intravenous catheters, urinary catheters; contact lenses; any kind of prosthetic implants such as heart valves, joint replacements, dental implants, and spinal implants, etc. . . . , or even on surfaces on non-medical devices such as pipes, tubes, towers, columns, etc. . . . .

In another further embodiment the invention relates to the use of an extract, or an active compound including naphtoquinones, anthraquinones, stereoisomeric forms, racemic mixtures, metabolites, esters or salts thereof, or mixtures thereof, as defined herein, or of a polar or apolar extract fraction, or a composition as defined herein for the preparation of a medicament for preventing and/or treating biofilm related diseases. In a further embodiment, the invention also provides a method for preventing and/or treating biofilm related diseases in an individual in need thereof, comprising administering an effective amount of one or more compounds selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein, or of a composition as defined herein.

The "individual", is generally a human subject, although as will be appreciated by those in the art, the patient may be animal as well. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of individual.

With a "biofilm related disease" is meant a disease which is associated with the formation of a biofilm. Such diseases may include, but are not limited to dental plaque, dental tartar and/or dental diseases related thereto as defined herein, acne, chronic wound infections, Cystic Fibrosis, urinary tract infections, ear infections, catheter related infections, etc. . . . .

In a further preferred embodiment the invention relates to the use of an extract, or an active compound including naphtoquinones, anthraquinones, stereoisomeric forms, racemic mixtures, metabolites, esters or salts thereof, or mixtures thereof, as defined herein, or of a polar or apolar extract fraction, or a composition as defined herein for the preparation of a medicament for preventing and/or treating dental plaque, dental tartar and/or dental diseases related thereto. In a preferred embodiment, the invention relates to method for preventing and/or treating dental plaque, dental tartar and/or dental diseases related thereto in an individual in need thereof, comprising administering an effective amount of one or more compounds selected from the group comprising an anthraquinone and a naphtoquinone, stereoisomeric forms, racemic mixtures, metabolites, esters or salts thereof, or mixtures thereof, or of a plant extract or active fraction thereof comprising said compound as defined herein, or of a composition as defined herein.

It shall be clear that the above-defined extract(s), active compound(s), active fraction(s), or composition(s) can also be applied on an advantageous way in other application fields of biofilm treating and EPS inhibition, but also in every general application field where the glucose transfer to a glucose polymer has to be inhibited. In an example of a bacterial application, the extract can be applied to inhibit e.g. bacterial glucosyltransferase in the production of muramine during the biosynthesis of the cell-wall of gram-positive bacteria. In another example of an anti-viral application, it can also be used for inhibition of the last phase of the viral replication when the viral capside proteins are glycosylated. In still another non microbial example it can also be applied for the inhibition of endogene glucosyltransferase in the context of the glucose and glycogene metabolism and for detoxification of the liver by glycosylation of glucurone acid by means of UPD-glucuronyltransferase.

EXAMPLES

Example 1

Influence of Plant Extracts on the Development of a S. mutans Biofilm

A first example illustrates the influence of extracts according to the invention on the development of a S. mutans biofilm. Hereby a model system for the study of biofilm formation on discs was used. The system comprises the irrigation of a growing medium and micro-organisms on discs and to develop the formation of microbial biofilms thereon. The system permits to compare biomasses of biofilms which were and were not exposed to plant extracts according to the invention.

Since teeth comprise hydroxyl apatite (HAP), discs comprising HAP (Clarkson Chromatography Products, South Williamsport, Pa., USA) were used for each experiment. The discs were applied in an in vitro continuous irrigating system with Modified Robbins Devices (MRD's; Tyler Research, Alberta, Canada). The MRDs were placed in an aluminium heater which is connected with acirculating hot water bath. The temperature of the bath was set to 37° C. The HAP discs were inoculated with a suspension of Streptococcus mutans cells (LMG 14558). Brain Heart Infusion Broth (BHI; BD, Franklin Lakes, N.J., USA) and Brain Heart Infusion Broth with 1% sucrose (=BHIS) were used as growing media.

Before starting biofilm experiments, the minimum inhibitory concentration (MIC value) was determined for each plant extract. All extracts were tested to a concentration below their MIC value. In this way, it can be concluded that an observed biofilm inhibition is not caused by a bactericidal effect of the plant extracts.

In experiments where a biofilm inhibitory effect of plant extracts was tested, 1% solutions of a plant extract in BHIS medium were always used. Hereby, the examined plant extract was added under aseptic conditions to the sterile BHIS solution. Quantification of biofilm formation was done by putting the HAP discs in a microtiter plate, followed by staining the discs with a SYTO®9 solution, that stains the DNA of living bacteria as well as of dead bacteria. After an incubation period of approximately 15 minutes the microtiter plate was scanned in an automatic microtiter plate reader (Wallac 1420 Multilabel Counter (Victor$^2$™; Perkin Elmer Life and Analytical Sciences, Boston, Mass., USA) able to measure absorption as well as fluorescence and luminescence.

It was shown that the average fluorescence of stained biofilm which were irrigated with BHIS was higher than the average fluorescence of biofilms which only had BHI as a nutrient. This shows that the presence of sucrose has a clearly positive effect on biofilm formation. Sucrose is converted into dextran which as a matrix stimulates the cell growth of S. mutans. From the experiments it could be concluded that dextran formation plays an essential role in the development of a thick mature biofilm. When this is inhibited, biofilm formation is also inhibited.

FIG. 1 illustrates the average fluorescence values of stained biofilms which were irrigated, during several experiments, with plant extracts according to the present invention. The results represented in this figure show that the fluorescence values for Amygdalus communis, Azadirachta indica (neem), Hypericum perforatum, Barosma betulina (Buchu), Rheum palmatum, Myrtus communis, Agnus castus, Punica granatum, Juglans regia, Centelia asiatica, Prunus dulcis, Solanum tuberosum, Citrus aurantium, Oenothea biennis, Eugenia caryophyllata, Chamomilla vulgaris, Acacia farnesiana, Jateorhiza palmata, Haematoxylon campechianum, Zea mais, Rumex acetosella, Uva-ursi arctostaphylos, Rubus idaeus, Woodfordia fruticosa, and Terminalia belerica are lower than 70% of the average fluorescence values of biofilms fed with BHIS. Fluorescence values below average indicate an inhibition of biofilm formation by the corresponding extracts. Average fluorescence values for Agnus castus, Myrtus communis, Punica granatum, Rumex acetosella, Terminalia belerica, Woodfordia fruticosa, and Zea mais, approach the average fluorescence value of BHI. It is remarkable that some extracts are active below the theoretical lower limit of BHI. Average fluorescence values with Citrus aurantium, Amygdalus communis dulcis, Azadirachta indica en Hyperi-

*cum perforatum, Rheum palmatum* are significantly lower than the average fluorescence values of BHI. It can therefore be concluded that the last-mentioned plant extracts are strong inhibitors of biofilm formation under the present test circumstances. These extracts are particularly suitable for inhibiting a non-sucrose dependent biofilm as well, and this without being bactericidal (since applied at sub-MIC values). This activity can be based on a specific interaction between the plant extracts and biofilm quorum sensing mechanisms. By means of such mechanisms micro-organisms regulate their number in a biofilm. It has surprisingly been shown that above-mentioned extracts are able to exert a disturbing activity on bacterial quorum sensing mechanisms.

Summarized, these experiments, which simulated the dynamic, biofilm forming oral circumstances for a series plant extracts, determined that extracts as mentioned above are able to inhibit sucrose dependent biofilm formation by *S. mutans* on hydroxyapatite discs. These plant extracts comprise, among others, extracts of *Amygdalus communis, Azadirachta indica, Hypericum perforatum, Barosma betulina, Rheum palmatum, Myrtus communis, Agnus castus, Punica granatum, Juglans regia, Centella asiatica, Prunus dulcis, Solanum tuberosum, Citrus aurantium, Oenothea biennis, Eugenia caryophyllata, Chamomilla vulgaris, Acacia farnesian, Jateorhiza palmata, Haematoxylon, Zea mais, Rumex acetosella, Arctostaphyllus uva-ursi, Rubus idaeus, Woodfordia fruticosa* and *Terminalia bellerica*.

Example 2

Inhibition of a Glycosyltransferase by Plant Extracts According to the Present Invention In a second example an anti-GTF activity for plant extracts according to the present invention is illustrated by means of an enzyme assay. Using an enzyme assay, it was shown that plant extracts according to the present invention have an inhibiting effect on glycosyltransferase (GTF) activity. The activity of glycosyltransferase is as follows: sucrose, derived from food, is bound on the active site of the enzyme and split into the monosaccharides fructose and glucose. The glucose remains bound to the GTF enzyme for a certain time and causes a conformational change of the protein. This spatial realignment of the enzyme enables a transfer from glucose to a dextran chain. The released fructose is absorbed and fermented by biofilm bacteria. The formed lactic acid is released and causes the deposit of minerals in the biofilm and gives rise to dental tartar formation. This forms an additional binding site for bacteria and thus results in an acceleration of dental diseases. In addition, lactic acid can dissolve (demineralize) the hydroxyl apatite of teeth, resulting in tooth decay and the formation of tooth cavities. Glucosyltransferases are mainly produced by *Lactobacillus* spp., *Leuconostoc* spp. and *Streptococcus* spp. GTF originating from *S. mutans* is known to have the highest activity and is a virulence factor in the pathogenesis of caries. The present assay showed that plant extracts according to the present invention have an inhibitory effect on the production of insoluble dextran, formed by the enzyme glucosyltransferase. Since the formed dextran is insoluble and gives rise to turbidity of a test medium, dextran formation can be followed in function of time by means of turbidity measurements.

In the present experiments a 10% sucrose-solution in 0.3 M acetate buffer was used at pH 5.5. Dextran sucrase of *Leuconostoc mesenteroides* (Sigma) was used as enzyme. This dextran sucrase is a glycosyl transferase that is very similar to the glycosyl transferase of *Streptococcus mutans*. All applied plant extracts were diluted to a 0.5% concentration. In these experiments TRIS (Sigma) dilutions (2 mM; 10 mM; 100 mM) and 1-deoxynojirimycine (DJM; Sigma) 10 mM were used as positive controls. The tested plant extracts comprise *Polygonum aviculare, Amygdalus communis dulcis (Prunus dulcis), Juglans regia, Acacia farnesiana, Cerasus vulgaris (Prunus cerasus), China rubra, Hypericum perforatum, Vitis vinifera, Eugenia caryophyllate, Sorbus aucuparia, Terminalia belerica, Rheum palmatum, Haematoxylum campechianum, Woodfordia fruticosa, Myrtus communis, Uva-ursi arctostaphylos, Prunus communis, Chimaphila umbellata, Hammamelis virginiana, Punica granatum*. On a microtiter plate two wells were filled with 100 μl sucrose-solution per tested plant extract. 90 μl of the extract was consequently added to both wells. Finally 10 μl of a GTF-solution was added in one of the wells and 10 μl MilliQ water in the other well (=blank). The turbidity was measured immediately at 690 nm by means of a microtiter plate reader, after which the microtiter plate was incubated at 30° C. on an orbital shaker. Measurements were repeated at fixed time points. From the difference in absorption between the blanks and GTF wells, the relative absorption of the formed dextran was calculated. Controls with acetate buffer without sucrose, but with the plant extract and GTF were measured. In every experiment three wells with GTF and sucrose solution without plant extract were also measured as negative control. A decrease in absorption was detected with different known inhibitors (TRIS and DJM) of GTF. Based herein, it was decided that the assay is suitable for detecting GTF inhibition and thus can be used to demonstrate GTF inhibition effected by plant extracts.

Figure 2:
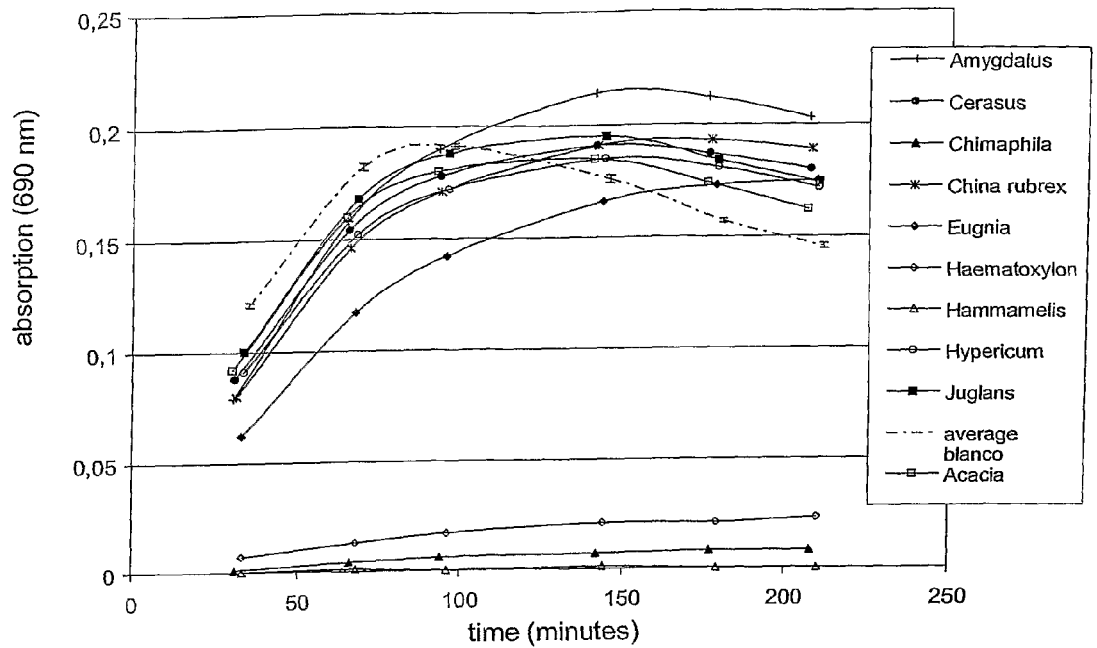
FIGS. 2 and 3 illustrate absorption of dextran, which is formed by GTF activity, in function of time at a 0.5% plant extract concentration of a number of plant extracts according to the present invention.
Figure 3:
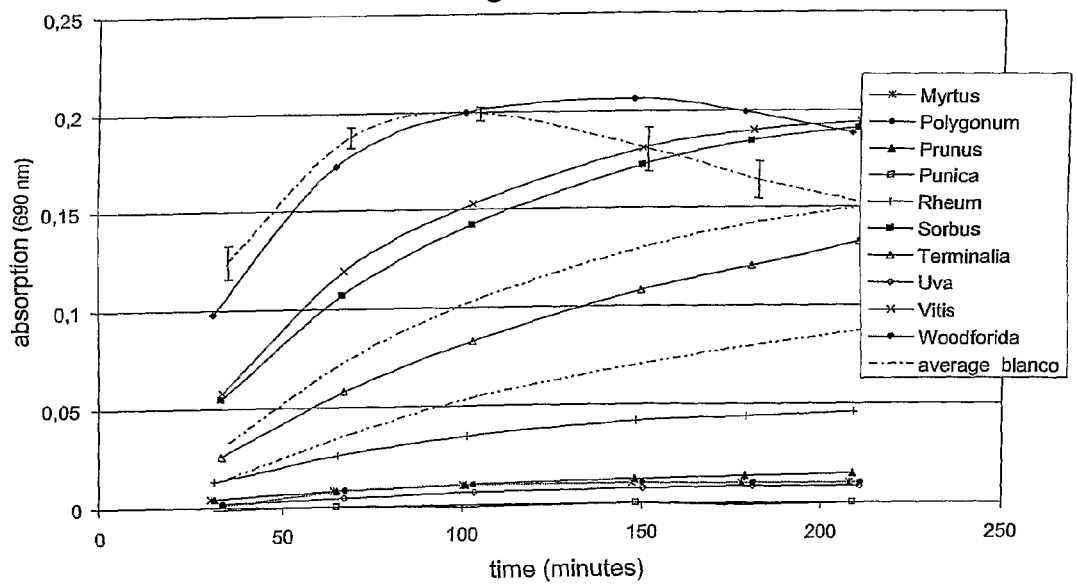

FIGS. 2 and 3 represent the absorption of dextran formed by GTF in function of time at a 0.5% plant extract concentration. These figures show that certain extracts according to the invention are able to inhibit GTF: the absorbance graphs of these extracts showed a changed course with respect to the blank graph.

Figure 5:
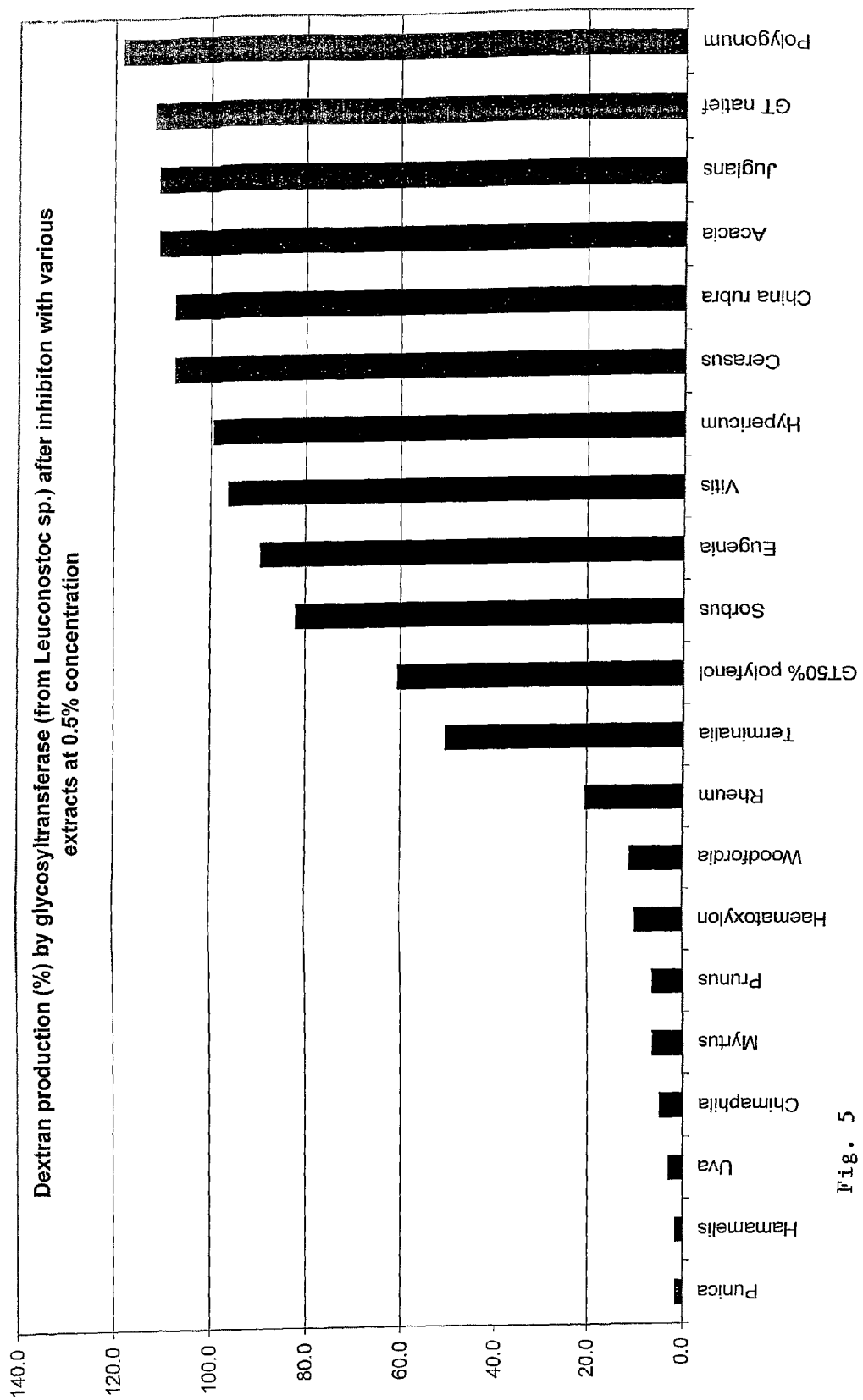
FIG. 5 illustrates the inhibition of dextran formation by a number of plant extracts according to the present invention at a 0.5% plant extract concentration.
Figure 6:
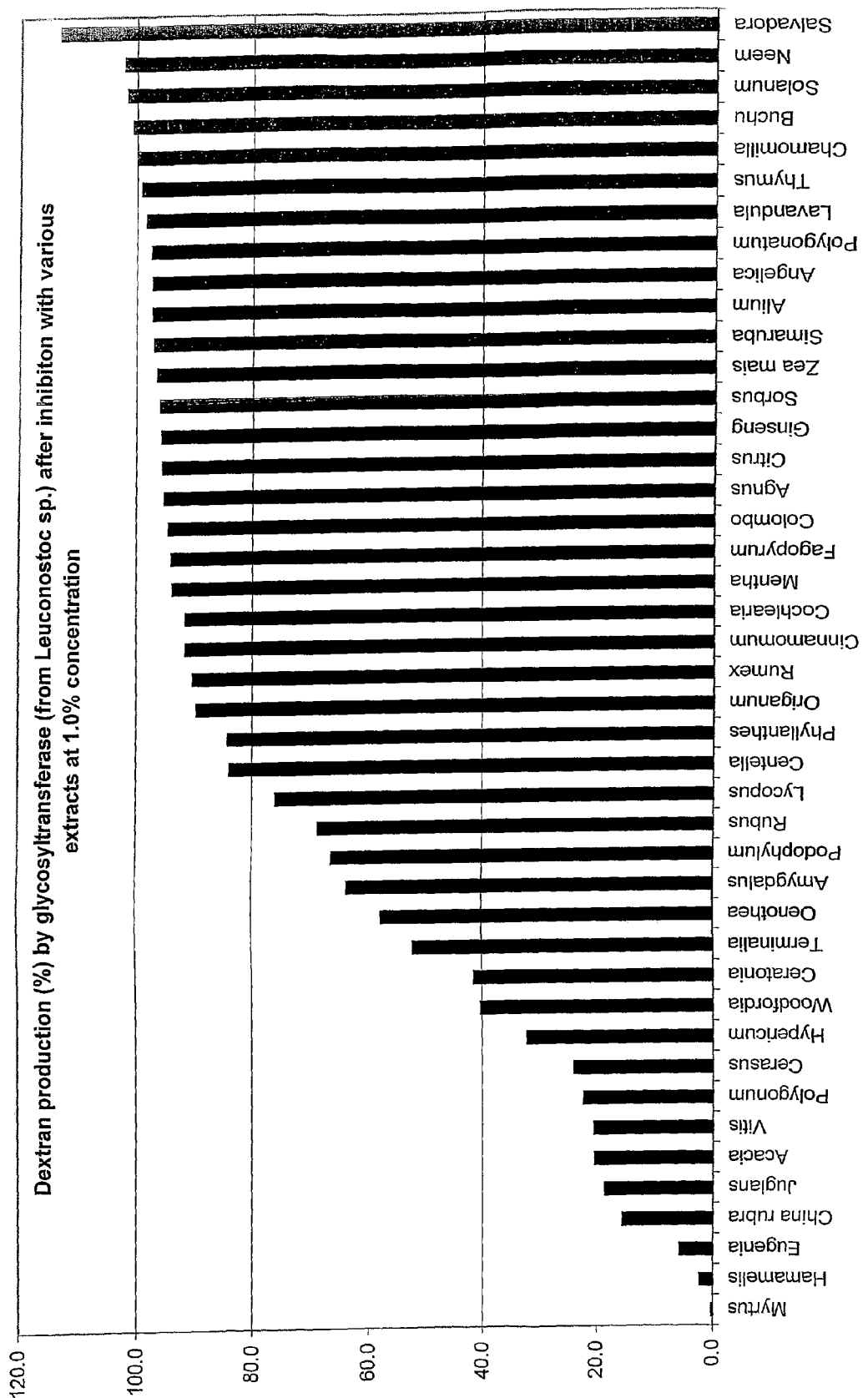
FIG. 6 illustrates the inhibition of dextran formation by a number of plant extracts according to the present invention at a 1% plant extract concentration.

FIGS. 5 and 6 illustrate the inhibition of dextran formation by some plant extracts according to the present invention respectively at a 0.5% plant extract concentration or at a 1% plant extract concentration. The figures represent dextran production (in %) by glycosyl transferase after inhibition with different extracts according to the present invention.

Summarized plant extracts were identified which are particularly appropriate to inhibit glucosyl transferase in an extremely effective way. More specifically it was shown that one or more of the following plants: in particular one of *Polygonum aviculare, Amygdalis communis dulcis (Prunus dulcis), Juglans regia, Acacia farnesiana, Cerasus vulgaris (Prunus cerasus), China rubra, Hypericum perforatum, Vitis vinifera, Eugenia caryophyllate, Terminalia belerica, Rheum palmatum, Haematoxylum campechianum, Woodfordia fruticosa, Myrtus communis, Uva-ursi arctostaphylos, Prunus communis, Chimaphila umbellata, Hammamelis virginiana, Punica granatum*, showed an effective anti-GTF activity.

Example 3

Classification of Plant Extracts

Figure 4:
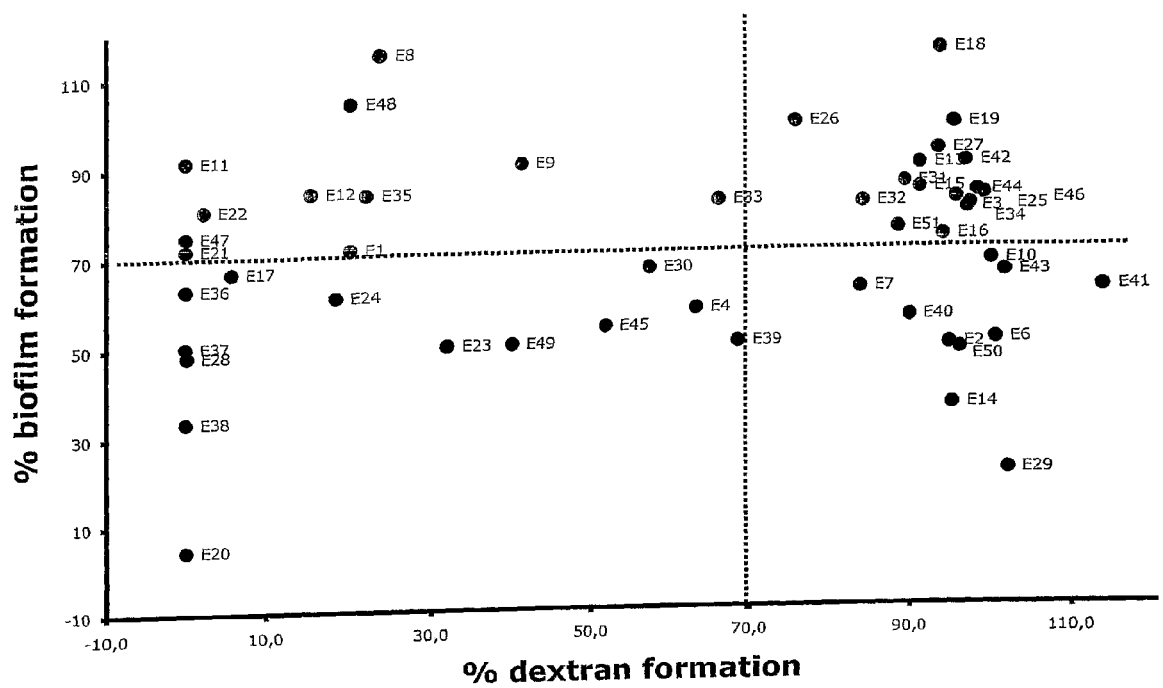
FIG. 4 represents a scatter plot of dextran inhibition and biofilm inhibition for different plant extracts according to the present invention.

In this example biofilm inhibition was tested for a number of plant extracts according to the present invention by a method as described in example 1 and dextran inhibition by a method described in example 2. Dextran inhibition was hereby measured at 1% sucrose and 1% extract. A scatter plot for dextran inhibition (measure for GTF inhibition) versus biofilm inhibition was established (FIG. 4). In this example plant extracts which showed an inhibition of dextran formation under an inhibition value of 80% were considered as GTF inhibitors. Plant extracts which showed an inhibition of biofilm formation under an inhibition value of 80% were considered as biofilm inhibitors. In FIG. 4 the numerical references refer to the following plant extracts: E1-*Acacia*, E2-*Agnus*, E3-*Alium*, E4-Amygdalus, E5-*Angelica*, E6-*Buchu*, E7-*Centella*, E8-*Cerasus*, E9-*Ceratonia*, E10-*Chamomilla*, E11-*Chimaphila*, E12-*China rubra*, E13-*Cinnamomum*, E14-*Citrus*, E15-*Cochlearia*, E16-*Jateorhiza*, E17-*Eugenia*, E18-*Fagopyrum*, E19-*Ginseng*, E20-GT50% polyphenol, E21-*Haematoxylon*, E22-*Hammamelis*, E23-*Hypericum*, E24-*Juglans*, E25-*Lavendula*, E26-*Lycopus*, E27-*Mentha*, E28-*Myrtus*, E29-*Neem*, E30-*Oenothea*, E31-*Origanum*, E32-*Phyllantes*, E33-*Podophylum*, E34-*Polygonatum*, E35-*Polygonum*, E36-*Prunus*, E37-*Punica*, E38-*Rheum*, E39-*Rubus*, E40-*Rumex*, E41-*Salvadora*, E42-*Simaruba*, E43-*Solanum*, E44-*Sorbus*, E45-*Terminalia*, E46-*Thymus*, E47-*Uva*, E48-*Vitis*, E49-*Woodfordia*, E50-*Zea mais*, E51-GT native.

From the plot two groups of plants can be derived: those plant extracts which essentially inhibit biofilm formation and act as GTF enzyme inhibitors, and those plant extracts which inhibit biofilm formation by an other, non GTF related activity.

A number of plant extracts were positioned on the zero value of the X-axis of FIG. 4. For these plant extracts, the dextran experiment was repeated under different conditions: dextran formation was measured at 10% sucrose and 0.5% extract. Results of this experiment are represented in FIG. 5. This shows that a number of extracts are remarkably more effective as GTF inhibitor than green tea (GT), and in particular extracts of the plants *Woodfordia, Punica, Hammamelis, Uva-ursi, Chimaphila, Myrtus, Prunus, Haematoxylon, Rheum* and *Terminalia*.

Example 4

Comparison of Activity of an Extract According to the Invention with Classical Oral Health Products This example illustrates the effect of some classical oral health products on the development of a *S. mutans* biofilm. Hereby, by analogy with example 1, a model system is used for the study of biofilm formation on little discs.

Figure 7:
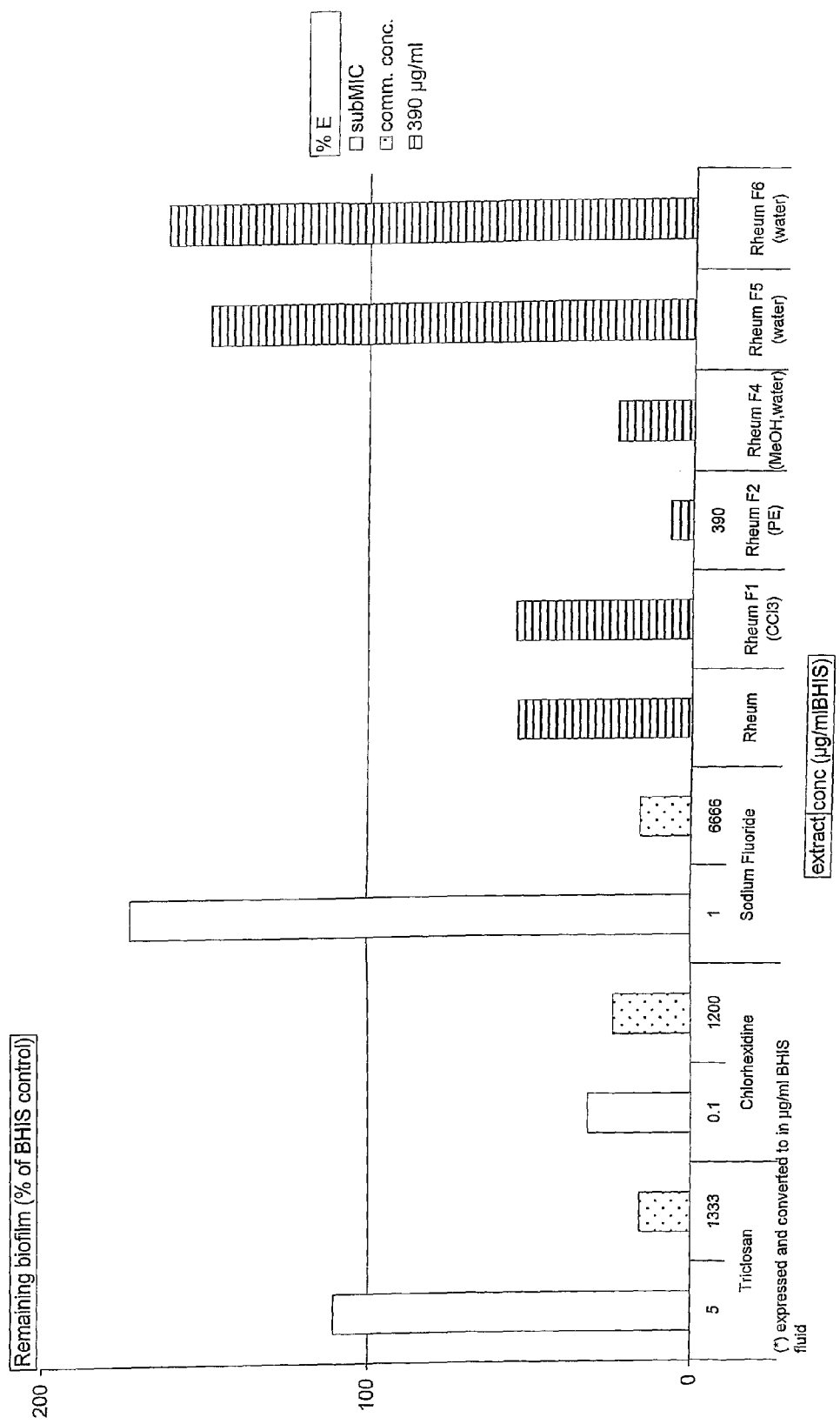
FIG. 7 illustrates the mean fluorescence values of stained biofilms irrigated by classical oral health products and different extracts of *Rheum*. Hereby sub-inhibitory and conventional concentrations were applied.

In a first experiment all oral health products were tested at a concentration below their minimal inhibitory concentration (MIC-value). As such, an observed biofilm inhibition is not due to a bactericidal effect of the products. such testing conditions also enables a comparison between the activity of these classical oral health products and extracts according to the present invention (example 1 and FIG. 1). FIG. 7 illustrates the average fluorescence values of stained biofilms that were irrigated by classical oral health products as triclosan, chlorohexidine and sodium fluoride tested at sub-MIC values. From the results it could be derived that the average fluorescence of stained biofilms, that were irrigated with classical oral health products, was higher than the average fluorescence of the biofilms that were obtained with plant extracts according to the invention (also example 1—FIG. 1). Comparison between the fluorescence value of these products and the ten best values that were noted down for extracts according to the invention (FIG. 1) and particularly for *Rheum* (FIG. 7), show that extracts according to the invention, and particularly a *Rheum* extract, show a greater biofilm inhibitory activity than specific classical oral health products at the tested concentrations, namely at a sub-MIC value. Comparison of the activity of additives to the activity of extracts according to the present invention at concentrations below a bactericidal value (MIC value) shows that classical additives at similar concentrations show no substantial activity, while extracts according to the present invention at this concentration already do show an effective biofilm inhibitory activity.

In a second experiment oral health products were tested at their commonly applied commercial dose in oral health products, for example in tooth paste. In this experiment also a *Rheum* extract was tested at this commercial concentration. This experiment enabled to make a comparison between the activity of these classical oral health agents and extracts according to the present invention (example 1) at a concentration which can be applied commercially. FIG. 7 illustrates the average fluorescence values of stained biofilms that were irrigated with classical oral health agents as triclosan, chlorohexidine and sodium fluoride; similar as for a *Rheum* extract. From the results it can be derived that *Rheum* extracts according to the invention show a similar biofilm inhibitory activity as the classical oral health agents at tested common commercial concentrations.

Example 5

Fractions of an Extract According to the Invention

Figure 8:
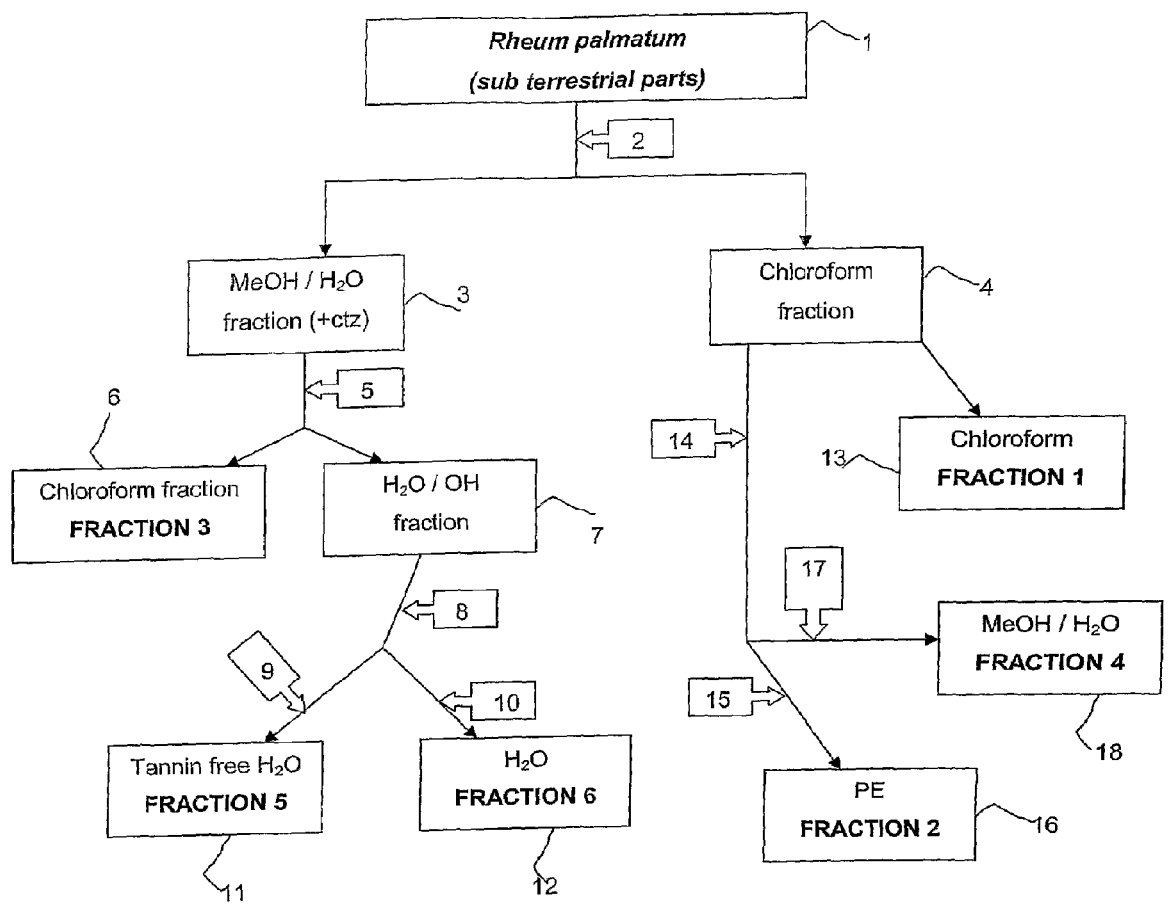
FIG. 8 illustrates a block diagram representing a method for obtaining different fractions of an extract according to the present invention.

In this example a number of fractions of a *Rheum* extract according to the present invention were prepared. In total, five fractions of the *Rheum* extract were obtained. The extraction method as applied in this example is schematically represented in FIG. 8. starting point was an extract of underground (sub terrestrial) parts of *Rheum palmatum*. From this 900 ml extract, 750 ml was dry-damped till 29.25 g dry matter (DS) and 150 ml was kept as reference, as indicated in block 1. The dry matter concentration of this starting material was 3.90%.

In a first step, indicated by 2, the dry damped material was dissolved in a 400 ml methanol/water solution (8:2), 2% citric acid (ctz) was added (pH 3). Then chloroform was added to obtain an emulsion. Hereof a methanol/water fraction (+citric acid) was separated and dry-damped, as indicated in block 3, and a chloroform fraction separated as indicated in block 4.

$NH_4OH$ was added to the methanol/water fraction (block 3) at a pH higher than 9 and then chloroform, as indicated in step 5. Hereby two fractions were obtained: a chloroform fraction obtained in block 6, which was named as FRACTION 3, but did not provide enough yield; and a water/OH fraction obtained in block 7. This last fraction was dry-damped in step 8 and then dissolved in methanol (16.4 g/400 ml). On the one hand 40 ml hereof (1.64 g DS) was separated in step 9 and brought on a polyamide column where after it was dry-damped. 1.58 g was then dissolved in water to obtain an aqueous fraction without tannins (FRACTION 5) in block 11 at a DS concentration of 3.95%. On the other hand 80 ml hereof was separated in step 10 and dry-damped. 3.3 g hereof was dissolved in 40 ml water to obtain an aqueous fraction (FRACTION 6) in block 12 at a DS concentration of 8.25%.

The chloroform fraction obtained in block 4 was dry-damped to 12.85 g DS. On the one hand 1.285 g DS hereof was weighted and dissolved in 20 ml methanol to obtain a chloroform fraction (FRACTION 1) at a concentration of 6.43% DS. On the other hand the remaining 11.565 g were dissolved in methanol/water (8:2) and petroleum ether (PE) in step 14. On the one hand a PE layer was separated en dry damped in step 15. Hereof 0.80 g was dissolved in 40 ml methanol to obtain a chloroform/PE fraction (FRACTION 2) in block 16 at a concentration of 2.00%. On the other hand a methanol/water layer was separated and dry-damped in step 17. Hereof 0.94 g was then dissolved in 40 ml water to obtain a chloroform/methanol fraction (FRACTION 4) in block 18 at a concentration of 2.35% DS.

Summarized five fractions were finally obtained, being: F1 (chloroform fraction), F2 (chloroform/petroleum ether fraction), F4 (chloroform/methanol fraction), F5 (water fraction without tannins), and F6 (water fraction with polyfenols and tannins).

The biofilm inhibitory activity of the F1, F2, F4, F5 and F6 fractions was further examined. Hereby, the effect of these different fractions on the development of a *S. mutans* biofilm was determined. Herefor, a model system was used by analogy with example 1 to study biofilm formation on little discs.

Results of these experiments are shown in FIGS. 1 and 7. In FIG. 1 the fractions at a concentration of 390 μg/ml (sub-MIC concentration) were compared with other fractions, *Rheum* starting material and green tea (GT) 50%. The results showed that apolar fractions of a *Rheum* extract (fractions 1, 2, and 4) show a good biofilm inhibitory activity. Polar fractions (fractions 5 and 6) were less active biofilm inhibitors (FIG. 1). From FIG. 7 it can also be derived that *Rheum*-F2 fraction showed a biofilm inhibitory action which was similar to that of classical oral health products as triclosan, chlorhexidine, and NaF, when these are tested at commercial concentrations (for example for fluor 1500 ppm as usual in tooth paste). FIG. 7 also showed that no biofilm inhibitory action could be measured for a polar fraction of a *Rheum* extract (fraction 5 and 6) under these test conditions.

It was further investigated whether the diverse fractions induce dextran inhibition. based on a method as described in example 2. Results of these experiments are summarized in table 1.

form extract was subjected to column chromatography on silica gel. Obtained fractions thereof were soluble in DMSO and analyzed in order to identify active compounds comprised herein. Several subfractions (fractions 1.1 to 1.20) were obtained. Several of these subfractions showed good biofilm inhibiting properties, for instance fraction 1.5 (see FIGS. 9-10). This subfraction 1.5 was subsequently further analyzed by means of a second extraction and liquid/liquid partition. A portion of fraction 1.5 was therefore subjected to column chromatography on silica gel and several subfractions were obtained (fraction 1.5.1 to 1.5.16). Several of these subfractions showed good biofilm inhibiting properties, for instance fraction 1.5.5—see FIG. 9).

In another experiment, root powder obtained from *Rheum* was extracted with petroleum ether to yield a petroleum ether extract, herein also referred to as fraction 2.2. This apolar PE fraction also showed good biofilm inhibiting properties, as illustrated on FIG. 9.

Figure 9:
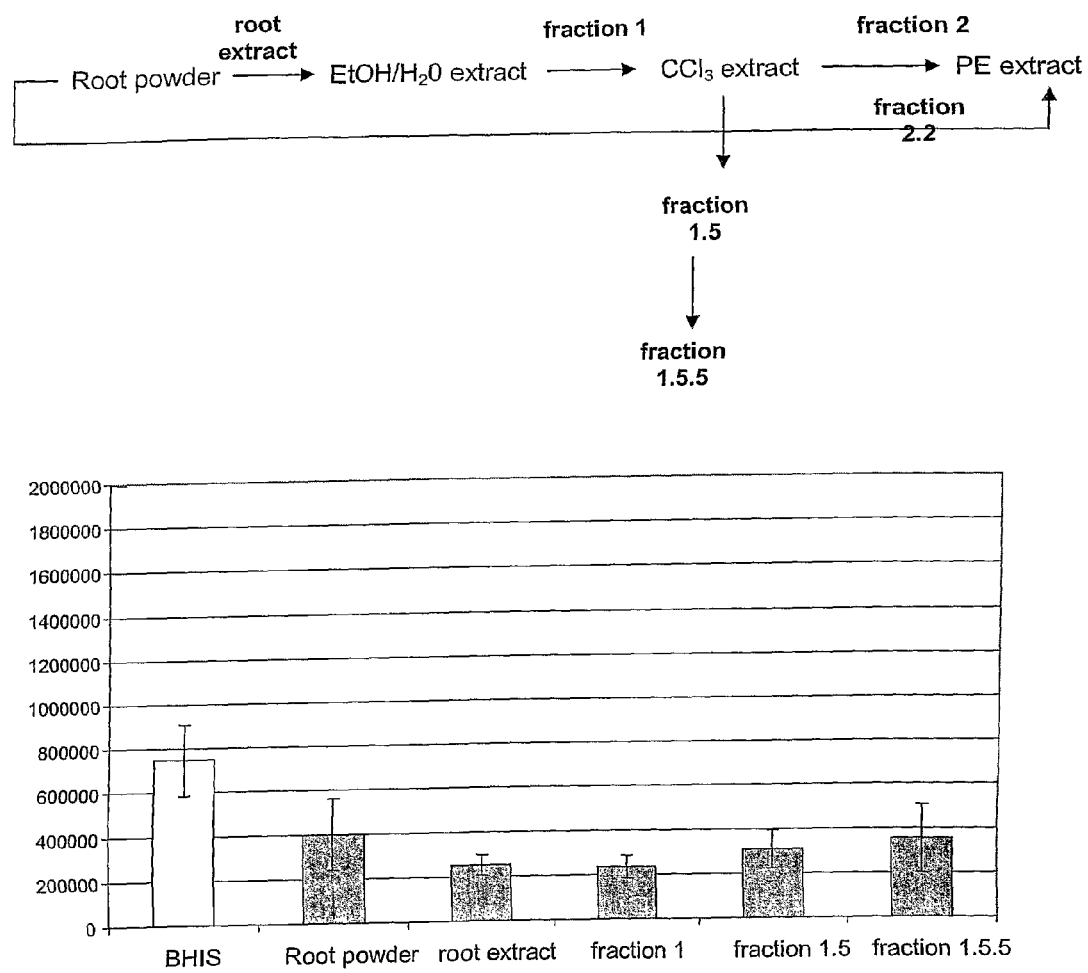
FIG. 9 illustrates fluorescence values indicative for a biofilm formation inhibitory activity obtained with root powder and extracts or fractions thereof obtained from a *Rheum* sp.

FIG. 9 illustrates a biofilm inhibiting activity of root powder and various extracts and subextracts obtained from *Rheum* sp. The figure illustrates that a root powder, a chloroform extract (fraction 1) and various subfractions thereof (fractions 1.5 and 1.5.5) show good biofilm inhibiting properties. Using these powder and extracts in biofilm experiments, as those explained in example 1, provided average fluorescence values which are significantly lower that those of the positive control BHIS.

Figure 10:
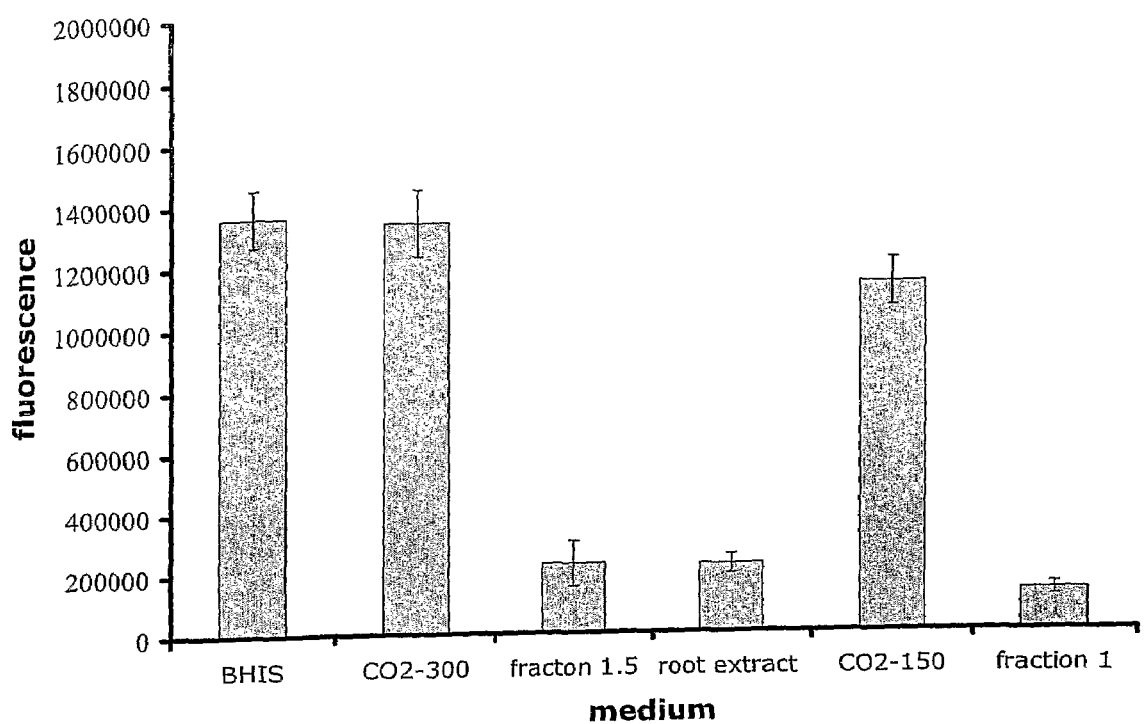
FIG. 10 illustrates fluorescence values indicative for a biofilm formation inhibitory activity obtained with extracts or fractions thereof obtained from a *Rheum* sp.

FIG. 10 illustrates a biofilm inhibiting activity of a rheum extract and fractions thereof. It was demonstrated that a rheum root extract, a chloroform extract thereof (fraction 1) and a subfraction thereof (fraction 1.5) show average fluores-

TABLE 1

Activity of some fractions of a Rheum extract according to the invention

| | Fraction | type | Conc (μg/ml) | Biofilm formation (%) | | GTF inhibition IC$_{50}$ value (%) |
|---|---|---|---|---|---|---|
| | Rheum | complete | 390 | + | 54% | 0.267 (avg) |
| F-1 | Chloroform | apolar | 390 | + | 54% | n |
| F-2 | Chloroform/petroleum ether | apolar | 390 | +++ | 7% | 1.479 |
| F-3 | | | no yield | | | |
| F-4 | Chloroform/methanol | apolar | 390 | ++ | 23% | 0.862 |
| F-5 | Water (tannin-free) | polar | 390 | — | 149% | n |
| F-6 | Water (polyfenoles and tannins) | polar | 390 | — | 162% | 0.309 |

Table 1 shows that the very active *Rheum*-F2 fraction showed minor GTF-inhibition. Fraction F6, which is aqueous and contains the tannins and polyfenols, is only slightly active in a biofilm experiment (FIG. 1), but very active as GTF-inhibitor. These results were further quantified by means of IC$_{50}$ values. The IC$_{50}$ values represent concentration of the extract (or fraction hereof) at which 50% of a cell population (i.e. bacteria) dies. The IC$_{50}$ values for *Rheum* F2, *Rheum* F4 and *Rheum* F6 were 1.479; 0.862 and 0.309(%) respectively. Summarized some particular fractions of the underground *Rheum* parts seem to give an almost complete inhibition of biofilm formation.

Example 6

Further Analysis of Apolar Plant Extract Fractions According to the Invention

In a further experiment, chloroform extract fraction 1, as disclosed in example 5, was further analyzed. Said chlorocence values which are significantly lower that those of the positive control BHIS. In this figure, $CO_2$ 300 and $CO_2$ 150 refers to the extract obtained by extraction with supercritical $CO_2$ at a pressure of 300 or 150 atm, respectively.

Figure 11:
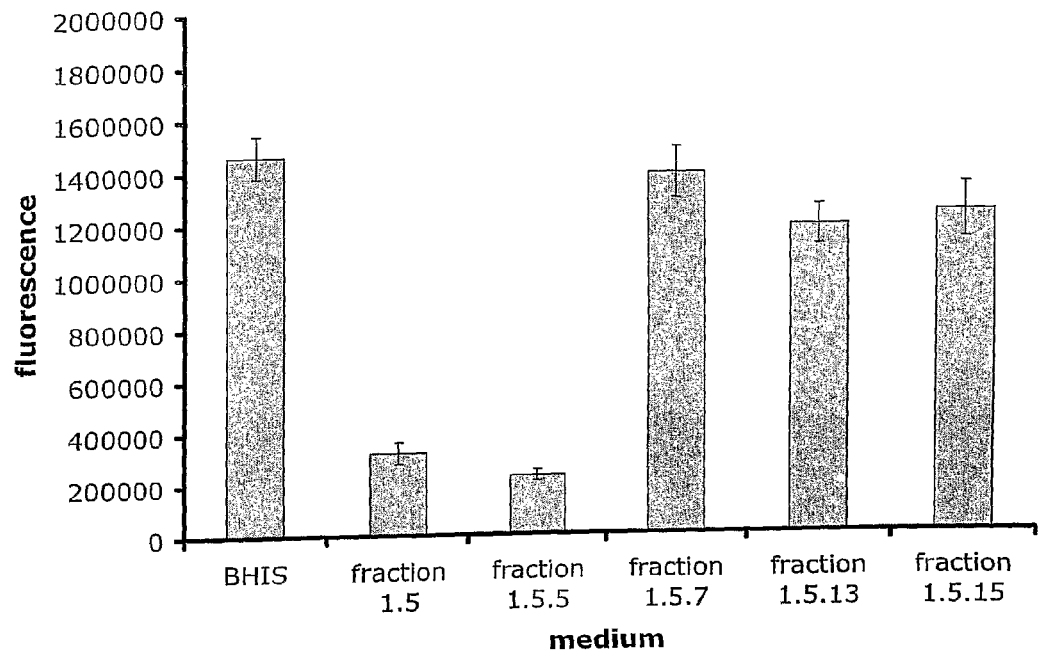
FIG. 11 illustrates a biofilm inhibiting activity of different subfractions of a chloroform extract from *Rheum* roots (fraction 1).

FIG. 11 illustrates a biofilm inhibiting activity of different subfractions of a chloroform extract from *Rheum* roots (fraction 1). Especially subfractions 1.5 and 1.5.5 show average fluorescence values which are significantly lower that those of the positive control BHIS. All extracts were used at a concentration of 5 μg/ml, except for the fraction 1.5, which is applied at a concentration of 50 μg/ml. These concentrations are all sub-MIC concentrations. This indicates that the extracts used in the indicated concentration do not provide anti-bacterial properties. At the indicated concentrations, no bacterial cell death is obtained.

Further analysis in accordance with the present experiments further showed that fractions and subfractions obtained as indicated above which showed good biofilm inhibiting properties comprised anthraquinones as active compounds, including aloe-emodin, chrysophenol and emodin.

Figure 12:
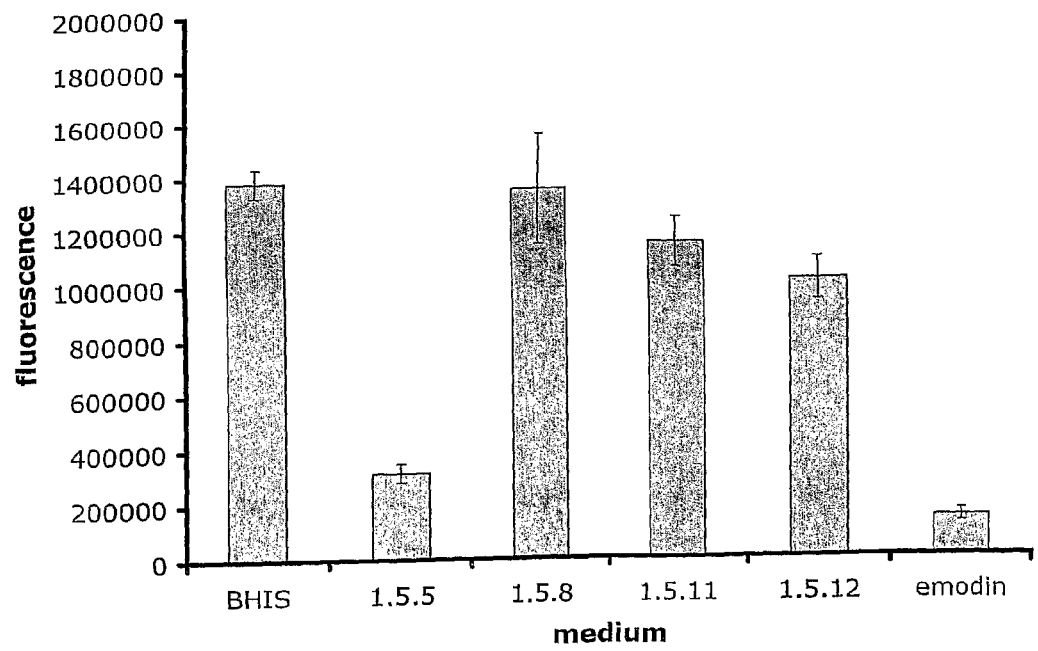
FIG. 12 illustrates a biofilm inhibiting activity of different subfractions of a chloroform extract from *Rheum* roots (fraction 1) and of emodin, an isolated active compound thereof.

FIG. 12 illustrates a biofilm inhibiting activity of different subfractions of a chloroform extract from *Rheum* roots (fraction 1) and of emodin, an isolated active compound thereof. As can be derived form the illustrated graph, especially subfraction 1.5.5 and the active compound emodin show average fluorescence values which are significantly lower that those of the positive control BHIS. All extract fractions and the emodin compounds were used at a concentration of 5 µg/ml. As indicated above, this concentration is a sub-MIC concentration and thus a non-bactericidal concentration.

It is particularly surprising that the present extracts or fractions thereof, or active compounds provided therein display excellent biofilm inhibiting properties without being bactericidal. The present extracts or fractions have a non-bactericidal mode of action, which is based on an induction of a non-lethal change of *S. mutans* membrane fluidity and/or interference with bacterial quorum sensing mechanisms.

Example 7

Biofilm Inhibiting Properties of Active Compounds According to the Invention

Figure 13:
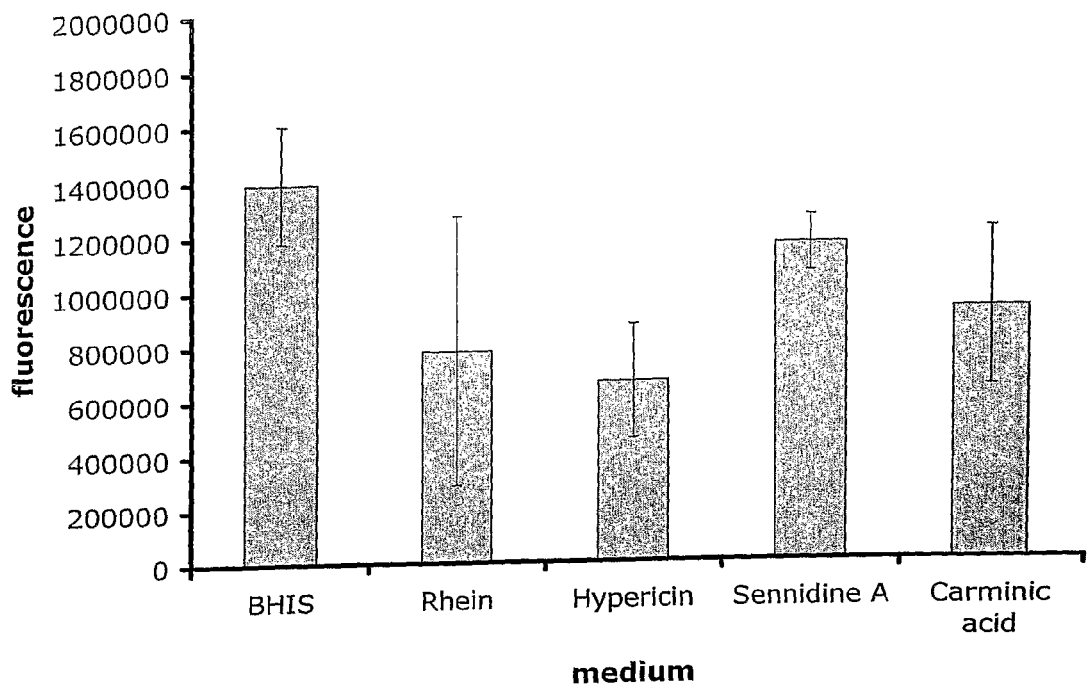
FIG. 13-16 illustrates a biofilm inhibiting activity of different anthraquinone and naphthoquinone compounds.
Figure 14:
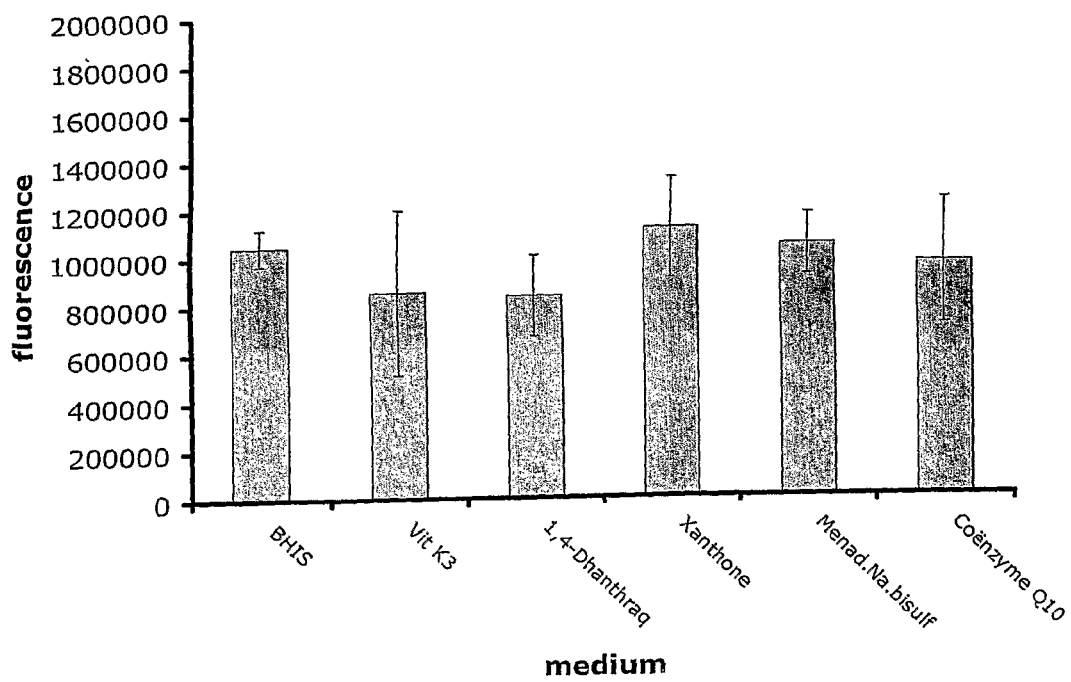
Figure 15:
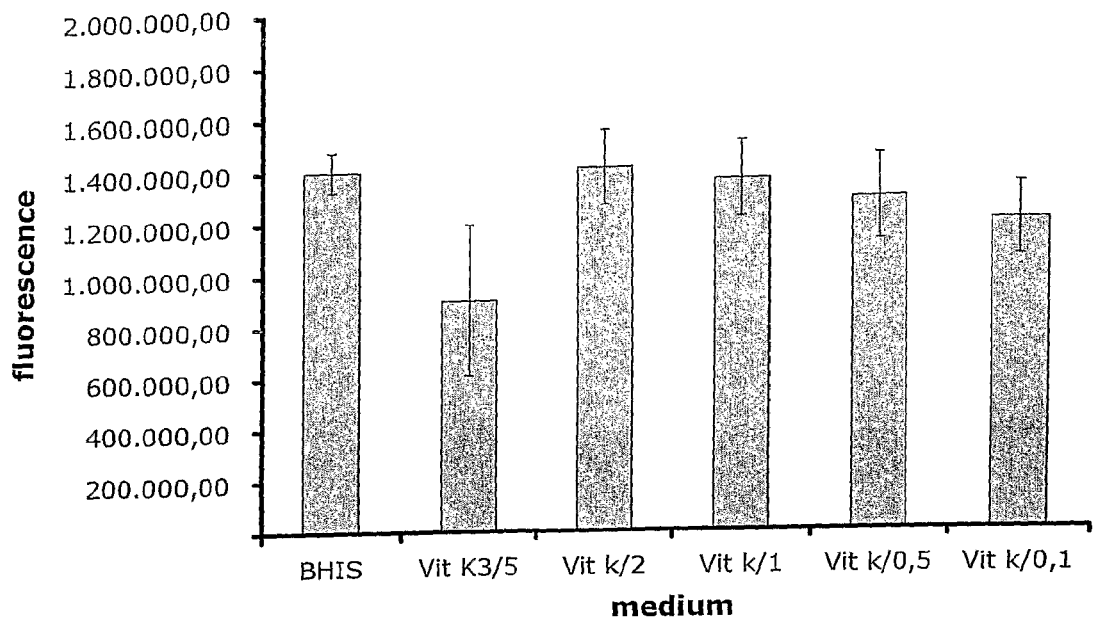
Figure 16:
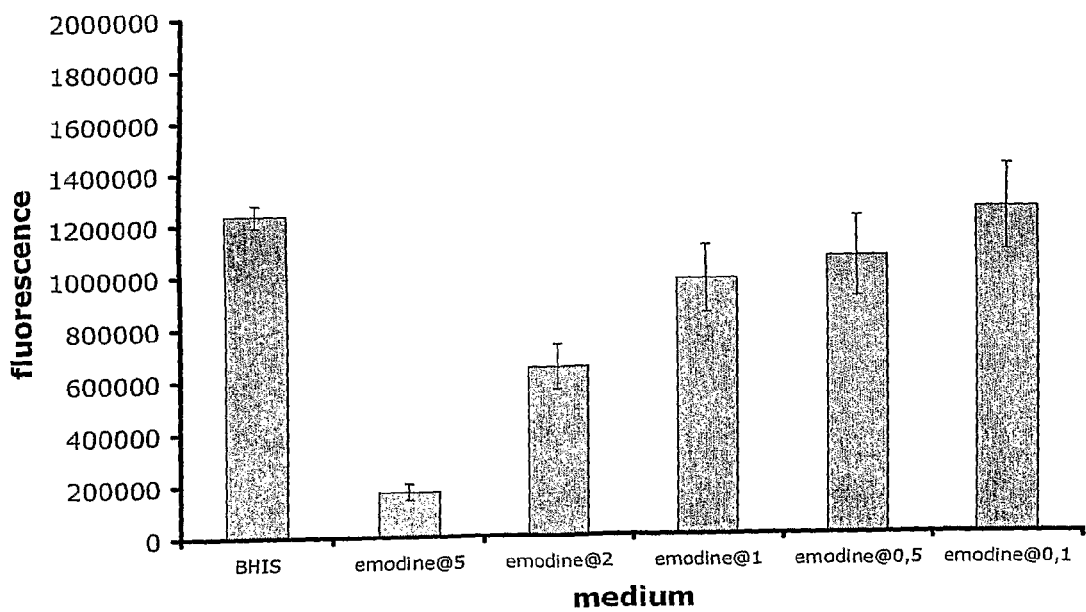

In this example several active compound selected from the group of compounds of the anthraquinones and the naphtoquinones were tested for biofilm inhibiting properties. FIG. 13-16 for instance illustrates a biofilm inhibiting activity of different anthraquinone and naphthoquinone compounds, including vitamin K3 and emodin. All compounds represented in FIGS. 13 and 14 were tested at a concentration of 5 µg/ml. FIG. 13 represents biofilm inhibiting properties of various compounds including rhein and carminic acid, which is a glucoside of 3,6,8-trihydroxy-1-methyl-9,10-dixox, 9-10, dihydroxyanthracene-2 carboxylic acid (a hydroxyathraquinone). FIG. 15 represents biofilm inhibiting properties of vitamin K3 at various concentrations which are sub MIC values and which range from 5, 2, 1, 0.5 to 0.1 µg/ml. FIG. 16 represents biofilm inhibiting properties of the anthraquinone emodin at various concentrations which are sub MIC values and which range from 5, 2, 1, 0.5 to 0.1 µg/ml.

Example 8

Examples of Oral Health Products

In another example some oral health products according to the invention and ingredients hereof are represented.

In an example an oral health product according to the invention comprises calcium or magnesium peroxide, sodium bicarbonate, ascorbic acid, colostrum, sodium lauryl sulphate, a plant extract according to the invention, and sweeteners, flavours, and menthol.

In another example an oral health product comprises water, cleaners/abrasives as e.g. chalk, calcium carbonate, dicalcium phosphate, dicalcium phosphate hydrate, sodium metaphosphate, silicic gel, aluminium oxyhydrates; absorbent agents such as glycerine or sorbitol; binding agents such as carboxymethylcellulose, carragene; flavours such as peppermint oil, aniseed oil, eucalyptus oil, menthol, spearmint oil (green mint); sweeteners such as saccharine, aspartame, xylose; solvents including oils such as sodium laurylsulphate, medicinal soap, fatty alcohol ethoxylate, betain, aminofluoride, quaternary ammonium compounds; preservatives such as PHB-esters, benzoic acids, chlorohexidine digluconate; colouring agents such as titan dioxide ("white pigment"); patent blue V; carmine red e.a.; therapeutic agents such as fluoride (sodium fluoride, sodium monofluoro phosphate, tin fluoride, amino fluoride); dental tartar inhibitors such as pyrophosphates, polyphosphates, phosphonates, sink citrate, vitamin A; vitamins, plaque inhibitors such as chlorohexidine, sanguinarine, triclosan and one or more plant extracts according to the present invention.

An extract according to the present invention is preferably applied in such oral health product in a amount ranging between 0.01 and 90% w/v; and for example between 0.5 and 70% w/v, and for example between 1.0 and 35% w/v, or between 1.5 and 25% w/v, or for example between 2.0 and 10% w/v.

In another example an oral health product comprises one or more of the above-indicated components may be provided which further includes one or more active compounds as defined herein, and preferably a vitamin K like compound and/or emodin. In a preferred embodiment, the active compound is applied in the oral health product at a concentration which is non bactericidal and preferably a concentration lower than the MIC value.

CONCLUSION

The present invention advantageously provides for compounds, compositions and methods for preventing and/or inhibiting biofilm formation or for treating biofilm without having to resort to bactericidal and/or antibiotic drugs with their accompanying disadvantages. In an example the final concentration is lower than or equal to 390 µg/ml (expressed in µg per ml growth medium on the Modified Robbins Device) for plant extracts and as low as 5 µg/ml (expressed in µg per ml growth medium on the Modified Robbins Device) for the present active compounds. When used at such concentration, the applied compounds have no bactericidal action.

What is claimed is:

1. An oral health product for preventing and/or inhibiting the formation of a biofilm in an oral cavity, dental plaque and/or dental tartar, said oral health product comprising a non bactericidal concentration of an apolar extract fraction of *Rheum palmatum*, wherein said apolar extract fraction is obtained by a method comprising:
   a) obtaining dried, subterrestrial plant parts of *Rheum palmatum*,
   b) contacting said dried subterrestrial plant parts with a methanol/water solution and a chloroform solution, thereby obtaining a methanol/water fraction and a chloroform fraction, whereby said chloroform fraction is separated,
   c) drying said chloroform fraction,
   d) contacting the dried chloroform fraction of step c) with a methanol/water solution and a petroleum ether (PE) solution, thereby obtaining a methanol/water fraction and a PE fraction, whereby said PE fraction is separated, and
   e) drying the PE fraction of step, wherein the dried PE fraction is said apolar extract fraction.

2. The oral health product according to claim 1, which is in the form of a gel, a paste, a gum, a stick pill, a rinsing liquid, a toothpaste, a strip, a chew, a tablet, soluble tablet, a topical medicament, an oral dentifrice, an injectable composition, an oral tablet, a lozenge, a soft gelatin capsule, a chewing gum, a chewing rod, a chewing bone, or a chewing strip.

3. A toothpaste for preventing and/or inhibiting the formation of a biofilm in an oral cavity, dental plaque and/or dental tartar comprising A) sorbitol, B) water and C) a non-bactericidal concentration of an apolar extract fraction of *Rheum palmatum*, wherein said apolar extract fraction is obtained by a method comprising:
- a) obtaining dried, subterrestrial plant parts of *Rheum palmatum*,
- b) contacting said dried subterrestrial plant parts with a methanol/water solution and a chloroform solution, thereby obtaining a methanol/water fraction and a chloroform fraction, whereby said chloroform fraction is separated,
- c) drying said chloroform fraction,
- d) contacting the dried chloroform fraction of step c) with a methanol/water solution and a petroleum ether (PE) solution, thereby obtaining a methanol/water fraction and a PE fraction, whereby said PE fraction is separated, and e) drying the PE fraction of step, wherein the dried PE fraction is said apolar extract fraction.

4. A mouth wash for preventing and/or inhibiting the formation of a biofilm in an oral cavity, dental plaque and/or dental tartar comprising A) water and B) a non-bactericidal concentration of an apolar extract fraction of *Rheum palmatum*, wherein said apolar extract fraction is obtained by a method comprising:
- a) obtaining dried, subterrestrial plant parts of *Rheum palmatum*,
- b) contacting said dried subterrestrial plant parts with a methanol/water solution and a chloroform solution, thereby obtaining a methanol/water fraction and a chloroform fraction, whereby said chloroform fraction is separated,
- c) drying said chloroform fraction,
- d) contacting the dried chloroform fraction of step c) with a methanol/water solution and a petroleum ether (PE) solution, thereby obtaining a methanol/water fraction and a PE fraction, whereby said PE fraction is separated, and
- e) drying the PE fraction of step, wherein the dried PE fraction is said apolar extract fraction.

* * * * *

UNITED STATES PATENT AND TRADEMARK OFFICE
CERTIFICATE OF CORRECTION

PATENT NO. : 7,691,418 B2  Page 1 of 3
APPLICATION NO. : 11/663119
DATED : April 6, 2010
INVENTOR(S) : Bart Rossel It is certified that error appears in the above-identified patent and that said Letters Patent is hereby corrected as shown below:

Title page, Column 2, Line 35, "and/or a naphtoquinone," should be changed to
--and/or a naphthoquinone--

Page 2, Column 2, Line 27, "Vitex-Agnus-Astus L." should be changed to --Vitex-Agnus-Castus L.--

Column 2, Line 3, "*sanguinis, S. mitis.*" should be changed to --*sanguinis, S. mitis,*--

Column 3, Line 15, "and a naphtoquinone," should be changed to --and a naphthoquinone,--

Column 3, Line 25, "and a naphtoquinone," should be changed to --and a naphthoquinone,--

Column 3, Lines 59-60, "and a naphtoquinone," should be changed to --and a naphthoquinone,--

Column 4, Line 3, "naphtoquinone, stereoisomeric" should be changed to
--naphthoquinone steroisomeric--

Column 4, Line 14, "and a naphtoquinone," should be changed to --and a naphthoquinone,--

Column 4, Line 24, "naphtoquinone, stereoisomeric" should be changed to
--naphthoquinone, stereoisomeric--

Column 6, Line 66, "and a naphtoquinone," should be changed to --and a naphthoquinone,--

Column 7, Line 29, "and a naphtoquinone," should be changed to --and a naphthoquinone,--

Column 8, Line 13, "release of bactericins" should be changed to --release of bacteriocins--

Column 9, Line 18, "of naphtoquinone" should be changed to --of naphthoquinone--

Column 9, Line 20, "physical an/or" should be changed to --physical and/or--

Column 11, Line 25, "and apiosyl," should be changed to --and apiosyl.--

Column 12, Line 40, "include vitamin K 1" should be changed to --include vitamin K1--

Column 12, Line 2, "napthoguinone and most" should changed to --naphthoquinone and most--

Column 12, Line 46, "a naphtoquinone, an" should be changed to --a naphthoquinone, an--

Signed and Sealed this

Twenty-fourth Day of August, 2010

David J. Kappos
*Director of the United States Patent and Trademark Office*

CERTIFICATE OF CORRECTION (continued)
U.S. Pat. No. 7,691,418 B2

Column 13, Line 56, "lucidin; lucidin;" should be changed to --lucidin;--

Column 14, Line 12, "triacetyidynemicin A;" should be changed to --triacetyldynemicin A;--

Column 14, Line 52, "altromycin 1, AM 8402;" should be changed to --altromycin I, AM 8402;--

Column 14, Line 54, "beta-imethylacrylshikonin;" should be changed to --beta-dimethylacrylshikonin;--

Column 15, Line 22, "Vitamin K 1;" should be changed to --Vitamin K1;--

Column 15, Line 26, "naphthoquione 2,3-epoxide;" should be changed to
--naphthoquinone 2,3-epoxide;--

Column 15, Line 38, "vitamin K1 chromenol;" should be changed to --vitamin K1 chromanol;--

Column 15, Line 38, "Vitamin K 3;" should be changed to --Vitamin K3;--

Column 16, Line 16, "*Terrminalia* sp.," should be changed to --*Terminalia* sp.,--

Column 17, Line 4, "*Terrminalia* sp.," should be changed to --*Terminalia* sp.,--

Column 17, Line 26, "*Rheum rabarbarum*" should be changed to --*Rheum rhabarbarum*--

Column 18, Line 6, "lignum, strobulus," should be changed to --lignum, strobilus,--

Column 19, Line 36, "as naphtoquinones," should be changed to --as naphthoquinone,--

Column 19, Line 39, "polyphenoles as" should be changed to --polyphenols as--

Column 19, Line 40, "catechins, anthocyans," should be changed to --catechins, anthocyanins,--

Column 20, Line 24, "*Terrminalia* sp.," should be changed to --*Terminalia* sp.,--

Column 20, Line 30, "*Terrminalia* sp.," should be changed to --*Terminalia* sp.,--

Column 21, Lines 23-24, "sodium monofluorphosphate," should be changed to
--sodium monofluorophosphate,--

Column 21, Line 24, "chlorehexidine," should be changed to --chlorhexidine,--

Column 22, Line 19, "agar, pectine," should be changed to --agar, pectin,--

Column 23, Line 51, "chlorehexidine, etc.," should be changed to --chlorhexidine, etc.,--

Column 23, Line 61, "in addition to" should be changed to --In addition to--

Column 24, Line 9, "bacteria, anchored." should be changed to --bacteria, anchored--

Column 24, Line 15, "chlorehexidine and" should be changed to --chlorhexidine and--

Column 28, Line 52, "*Centelia asiatica*," should be changed to --*Centella asiatica*,--

Column 29, Line 26, "*Arctostaphyllus uva-ursi*," should be changed to --*Arctostaphylos uva-ursi*,--

Column 30, Line 3, "and 1-deoxynojirimycine" should be changed to --and 1-deoxynojirimycin--

CERTIFICATE OF CORRECTION (continued)
U.S. Pat. No. 7,691,418 B2

Column 30, Line 8, "*Eugenia caryophyllate,*" should be changed to --*Eugenia caryophyllata,*--

Column 30, Line 48, "*Amygdalis communis*" should be changed to --*Amygdalus communis*--

Column 30, Line 49, "*Acacia famesiana,*" should be changed to --*Acacia farnesiana,*--

Column 30, Line 50, "*Eugenia caryophyllate*" should be changed to --*Eugenia caryophyllata,*--

Column 31, Line 51, "such testing" should be changed to --Such testing--

Column 31, Line 55, "chlorohexidine and" should be changed to --chlorhexidine and--

Column 32, Lines 16-17, "chlorohexidine and" should be changed to --chlorhexidine and--

Column 32, Line 31, "starting point was" should be changed to --Starting point was--

Column 33, Line 7, "with polyfenols and" should be changed to --with polyphenols and--

Column 33, line 29, "dextran inhibition." should be changed to --dextran inhibition--

Columns 33-34, Table 1, Line 12, "F-6   Water (polyfenoles" should be changed to
 --F-6   Water (polyphenols--

Column 33, Line 51, "and polyfenols," should be changed to --and polyphenols,--

Column 35, Line 2, "chrysophenol and emodin." should be changed to --chrysophanol and emodin.--

Column 35, Lines 36-37, "(a hydroxyathraquinone)." should be changed to
 --(a hydroxyanthraquinone).--

Column 35, Line 64, "ethoxylate, betain," should be changed to --ethoxylate, betaine,--

Column 35, Line 66, "chlorohexidine digluconate;" should be changed to --chlorhexidine digluconate;--